US009889240B2

United States Patent
Locke et al.

(10) Patent No.: US 9,889,240 B2
(45) Date of Patent: *Feb. 13, 2018

(54) SYSTEM AND METHOD FOR MANAGING REDUCED PRESSURE DELIVERED TO A TISSUE SITE

(71) Applicant: KCI Licensing, Inc., San Antonio, TX (US)

(72) Inventors: Christopher Brian Locke, Bournemouth (GB); David Robson Blandford, Fordingbridge (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,620

(22) Filed: Oct. 7, 2016

(65) Prior Publication Data

US 2017/0035948 A1   Feb. 9, 2017

Related U.S. Application Data

(63) Continuation of application No. 13/451,384, filed on Apr. 19, 2012, now Pat. No. 9,474,838.
(Continued)

(51) Int. Cl.
*A61M 1/00* (2006.01)
*A61M 5/178* (2006.01)
(Continued)

(52) U.S. Cl.
CPC ........ *A61M 1/0033* (2014.02); *A61M 1/0066* (2013.01); *A61M 1/0088* (2013.01)

(58) Field of Classification Search
CPC .......... A61M 1/00; A61M 5/178; A61M 5/00; A61M 5/32; A61M 35/00; A61F 13/00
See application file for complete search history.

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Tatyana Zalukaeva
*Assistant Examiner* — Ilya Treyger

(57) ABSTRACT

An apparatus and method for managing reduced pressure at a tissue site are disclosed. The apparatus comprises a pump for supplying reduced pressure to the tissue site, a motor coupled to the pump to propel the pump, and a drive system electrically coupled to the motor that includes a power source that provides a source of direct current power to the motor during an operational period at a substantially constant current and of sufficient magnitude to supply a targeted reduced pressure during the operational period. The drive system also includes a controller that monitors the pump's loading on the motor by measuring the voltage across the motor to determine whether the motor voltage remains within a predetermined operational range of voltages necessary for maintaining the reduced pressure supplied by the pump proximate to the targeted reduced pressure without
(Continued)

directly measuring the reduced pressure using a pressure sensor.

36 Claims, 10 Drawing Sheets

Related U.S. Application Data

(60) Provisional application No. 61/477,406, filed on Apr. 20, 2011.

(51) Int. Cl.
*A61M 5/00* (2006.01)
*A61M 5/32* (2006.01)
*A61M 35/00* (2006.01)
*A61F 13/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewell |
| 5,607,388 A | 3/1997 | Ewell |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1954 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

(56) References Cited

FOREIGN PATENT DOCUMENTS

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnki Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English thereof translation.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D, et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp, 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P, et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al, (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G, Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S,R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines; A Reference Source for Clinicians; Jul. 2007.

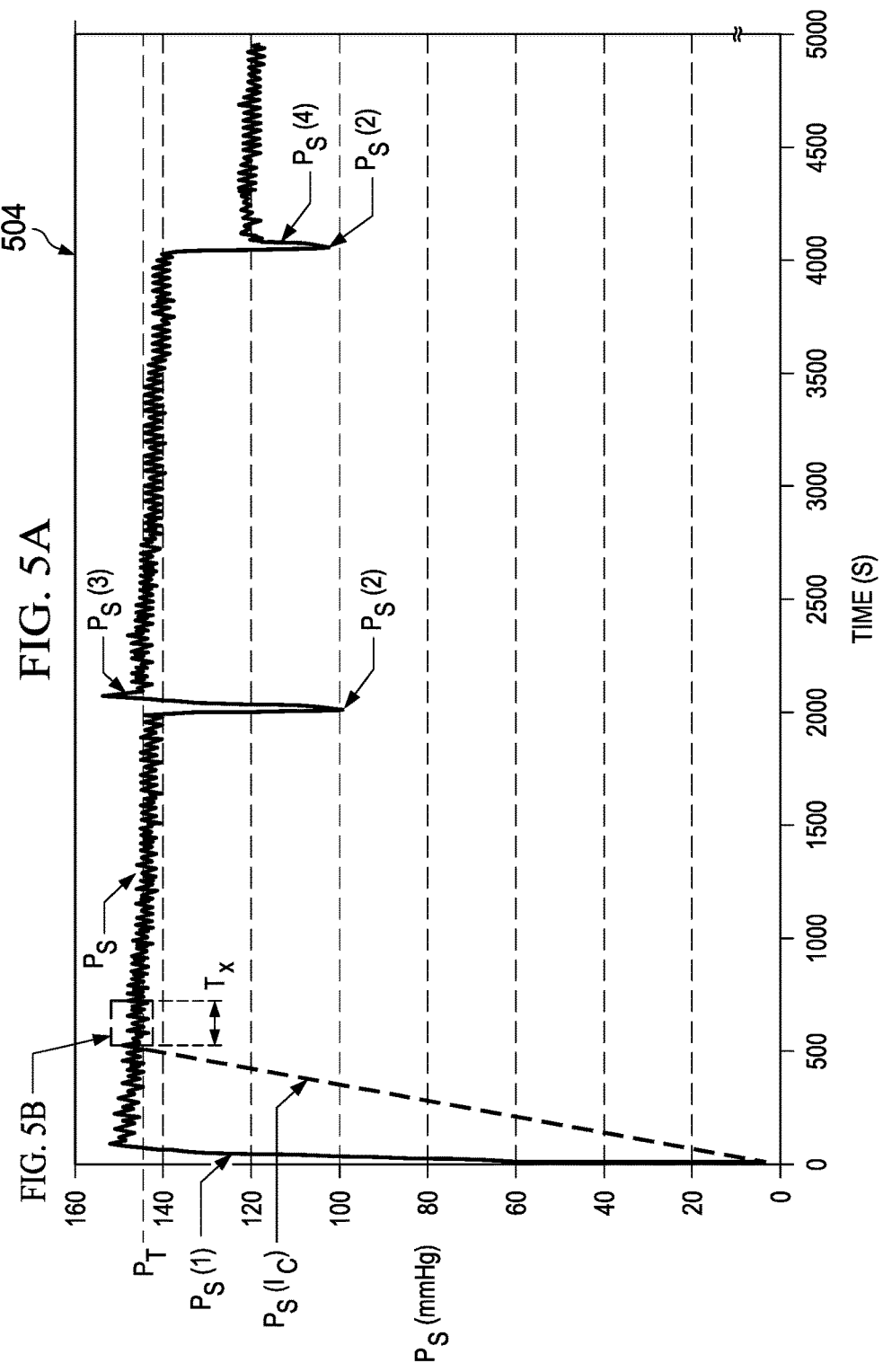

SYSTEM AND METHOD FOR MANAGING REDUCED PRESSURE DELIVERED TO A TISSUE SITE

RELATED APPLICATIONS

This application is a continuation of U.S. patent application Ser. No. 13/451,384, filed Apr. 19, 2012, which issued as U.S. Pat. No. 9,474,838 on Oct. 25, 2016, which claims the benefit, under 35 U.S.C. §119(e), of the filing of U.S. Provisional Patent Application No. 61/477,406, filed Apr. 20, 2011, which is incorporated herein by reference for all purposes.

BACKGROUND OF THE INVENTION

1. Field of the Invention

The present invention relates generally to the field of tissue treatment, and more specifically to a system and method for applying reduced pressure delivered to a tissue site.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. The treatment of wounds using reduced pressure is sometimes referred to in the medical community as "negative pressure tissue treatment," "reduced pressure therapy," or "vacuum therapy." This type of treatment provides a number of benefits, including faster healing, and increased formulation of granulation tissue.

The reduced pressure at a tissue site caused by a reduced pressure treatment system may need to be properly managed to increase the effectiveness of the reduced pressure treatment. In addition, leaks and blockages in the components of the reduced pressure treatment system may need to be detected and corrected to maintain effective treatment. For example, a leak or blockage in the tube that connects a reduced pressure source, such as a vacuum pump, to the tissue site may disrupt the reduced pressure treatment being administered to the tissue site. The management or control of reduced pressure treatment systems may be generally referred to as "pump pressure control" or "differential pressure control."

In one currently used pump pressure control system, pressure is measured at the pump outlet, i.e., the "supply pressure," and fed into a control system that drives a pump to achieve a target pressure at the outlet of the pump. Such control systems utilize a pressure sensor to measure the supply pressure being delivered at the outlet of the pump. Another currently used pump pressure control system also measures the pressure in proximity to the tissue site, i.e., the "applied pressure" utilizing a second pressure sensor close to the tissue site. A control system may be also programmed to compare the supply pressure to the applied pressure to determine the difference in pressure, i.e., the "applied differential pressure" between them. The applied differential pressure provides information about leaks or blockages that occur between the tissue site and the pump.

Currently used differential pressure control systems employ two sensors to measuring pressure at both the pump outlet and at the tissue site. The pressures measured by the two sensors are compared so that the occurrence of leaks or blockages in reduced pressure treatment system may be identified. However, the two sensors used by current differential pressure control systems increase the size, weight, cost, and complexity of such systems. For example, the use of two sensors increases the amount of electronic circuitry and power used by the reduced pressure treatment system. In addition, comparing measurements from two different sensors requires that the reduced pressure treatment system include circuitry and software for making the comparison. The additional components required by current differential pressure control systems reduce the ability of those systems to be used to treat low-severity wounds and wounds on ambulatory patients. In addition, the additional components required by such systems increase the obtrusiveness and weight of the reduced pressure treatment system, thereby increasing the discomfort and limiting the mobility of the patient. Discrete pressure sensors for providing feedback to the system are not only expensive, but also increase the potential for wound infection as another input connected to the pneumatic circuit of the negative pressure wound care system.

BRIEF SUMMARY OF THE INVENTION

To alleviate the existing problems with reduced pressure treatment systems, the illustrative embodiments described herein are directed to an apparatus and method for managing reduced pressure delivered to a tissue site and, more specifically, an apparatus and method for controlling the supply pressure without using a pressure sensor. The apparatus includes a reduced pressure source comprising a motor that drives a pump to generate reduced pressure. The reduced pressure is delivered to the tissue site via a delivery tube. The apparatus includes a controller that provides a constant current to the pump motor and monitors the voltage across the motor to ascertain and control the supply pressure without the use of a pressure sensor. The manufacturer of such a controller or a care-giver sets a target pressure and other parameters for the controller to deliver and control the supply pressure as the reduced pressure therapy that is applied to the tissue site. A pressure sensor may be used to measure the applied pressure for the purposes of computing a differential pressure as described above, but is not necessary for the purposes of the illustrative embodiments described herein.

One illustrative embodiment provides an apparatus for managing reduced pressure delivered to a tissue site. The apparatus comprises a pump for supplying reduced pressure for application of reduced pressure to the tissue site that varies over time, and a motor coupled to the pump to propel the pump at speeds varying with the reduced pressure. The motor may be a direct current (DC) motor or an alternating current (AC) motor driven by an inverter that converts direct current to alternating current for the AC motor, both referred to as a DC-driven motor. In either case, the apparatus further comprises a drive system electrically coupled to the motor that includes a power source that provides a source of direct current power to the motor during an operational period at a substantially constant current and of sufficient magnitude to supply a targeted reduced pressure during the operational period. The drive system also includes a controller that monitors the pump's loading on the motor by measuring the voltage across the motor to determine whether the motor voltage remains within a predetermined operational range of voltages necessary for maintaining the reduced pressure supplied by the pump proximate the targeted reduced pressure without directly measuring the reduced pressure using a pressure sensor.

The illustrative embodiments also include drive systems that perform functions when the measured voltage is outside the predetermined operational range of voltages. In one embodiment, the measured motor voltage may drop below the operational range of voltages inferentially indicating that the supply pressure is proximate the targeted pressure so that the drive system disconnects the motor from the constant current source. In another embodiment, the measured motor voltage may spike above the operational range of voltages inferentially indicating that the supply pressure has dropped below the targeted pressure as a result of a significant leak so that the drive system increases power to the motor to run faster and compensate for the pressure loss if possible. The drive system performs other functions in addition to these embodiments.

The illustrative embodiments also provide a method for managing reduced pressure delivered to a tissue site. The process provides a constant current to a pump motor and measures the voltage across the motor to ascertain and control the supply pressure. The process ascertains and controls the supply pressure based on a target pressure and other parameters set by the patient or a care-giver. The process performs reduced pressure management functions based on the comparison.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 5A is a graph illustrating pressure control of a motor-drive system in accordance with an illustrative embodiment of the present invention wherein the x-axis represents time in seconds(s) and the y-axis represents pressure generated by a pump in Torr (mmHg) that varies with time;

DETAILED DESCRIPTION OF THE PREFERRED EMBODIMENT

Figures 1, 1A:
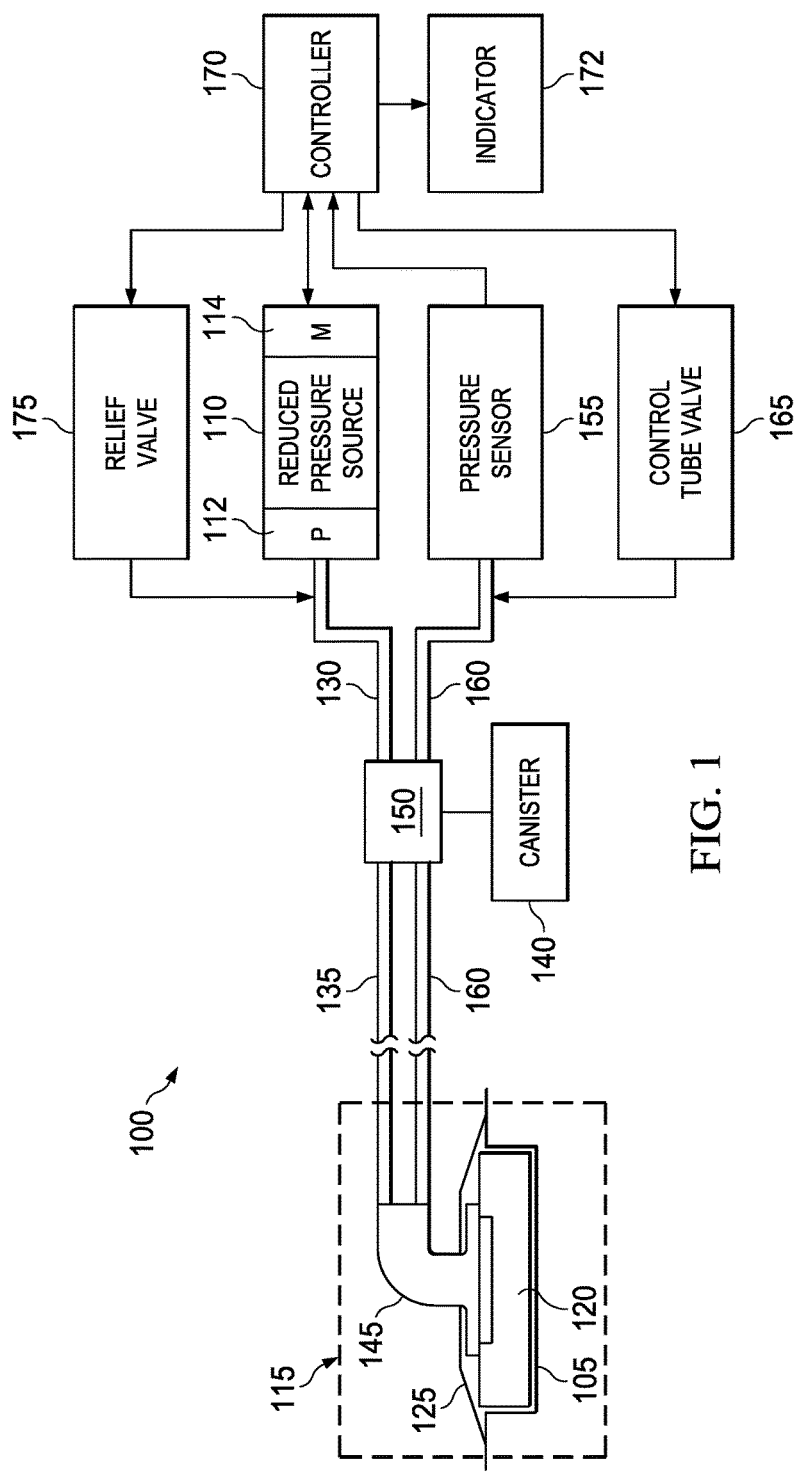
FIG. 1 is a block diagram of an apparatus for managing reduced pressure at a tissue site in accordance with an illustrative embodiment of the present invention.
FIG. 1A is a perspective view of a multi-lumen tube in accordance with an illustrative embodiment of the invention.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The illustrative embodiments described herein provide and apparatus and method for managing reduced pressure delivered to a tissue site. Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

The apparatus includes a reduced pressure source that generates reduced pressure. A reduced pressure source is any device capable of generating reduced pressure. In one embodiment, the reduced pressure source comprises a motor and pump wherein the motor drives the pump to generated the reduced pressure. The reduced pressure is delivered to the tissue site via a delivery tube. The apparatus may also include a pressure sensor which is any device capable of measuring or detecting a pressure. The pressure sensor detects an actual reduced pressure at the tissue site, i.e., the applied pressure. The pressure sensor for measuring the applied pressure is the only pressure sensor included in the apparatus, although the pressure sensor is not necessary for operation of the system.

The apparatus also includes a controller. A controller is any device capable of processing data, such as data from the pressure sensor. A controller may also control the operation of one or more components of the apparatus. The controller also provides a constant current to the motor of the reduced pressure source and monitors the voltage across the motor to ascertain and control the supply pressure generated by the pump. In one embodiment, the reduced pressure source generates a decreased supply pressure when the applied pressure at the tissue site detected by the pressure sensor exceeds a target pressure. In another embodiment, the reduced pressure source generates an increased supply pressure when a target pressure exceeds the applied pressure at the tissue site detected by the pressure sensor.

The apparatus may also include a relief valve coupled to the delivery tube. A relief valve is any valve capable of decreasing the reduced pressure. In this embodiment, the relief valve may open to decrease the applied pressure at the tissue site when the applied pressure detected by the single pressure sensor exceeds a target pressure by a predetermined threshold.

As used herein, the term "coupled" includes coupling via a separate object. For example, the relief valve may be coupled to the delivery tube if both the relief valve and the relief tube are coupled to a third object. The term "coupled" also includes "directly coupled," in which case the two objects touch each other in some way. The tem' "coupled" also encompasses two or more components that are continuous with one another by virtue of each of the components being formed from the same piece of material.

The apparatus includes an indicator. An indicator is any device capable of emitting a signal. For example, the indicator may emit a signal to a user of the apparatus, e.g., the patient or a care-giver. The indicator emits a signal when the controller determines that the applied pressure measured by the single pressure sensor is nonresponsive to the increase in supply pressure generated by the reduced pressure source. "Nonresponsive" may refer to the lack of an effect on the applied pressure, as measured by the pressure sensor, from an increase in supply pressure generated by the reduced pressure source. Additional details regarding the responsiveness of the applied pressure measured by the single pressure sensor are provided in the illustrative embodiments described below.

The illustrative embodiments also provide a method for managing reduced pressure delivered to a tissue site. The process determines a target pressure. The target pressure may be any reduced pressure that is set by a user or the apparatus, such as the controller. The process detects the applied pressure at the tissue site using a pressure sensor. The process provides a constant current to a pump motor and monitors the voltage across the motor to ascertain and control the supply pressure. The process ascertains and controls the supply pressure based on a target pressure and other parameters set by the patient or a care-giver. The process performs a reduced pressure management function based on the comparison. The process performs a reduced pressure management function based on the comparison. A reduced pressure management function is any operation, function, or activity of any or all of the components of the apparatus. A reduced pressure management function may also be performed by a user.

In one embodiment, performing the reduced pressure management function based on the comparison includes decreasing a generated reduced pressure generated by a reduced pressure source in response to the actual reduced pressure exceeding the target reduced pressure. In another embodiment, the process opens a relief valve that decreases the actual reduced pressure at the tissue site in response to the actual reduced pressure exceeding the target reduced pressure by a predetermined threshold. In another embodiment, the process eliminates the generated reduced pressure by turning off the reduced pressure source in response to the actual reduced pressure exceeding the target reduced pressure by a predetermined threshold.

In another embodiment, performing the reduced pressure management function based on the comparison includes increasing a generated reduced pressure generated by a reduced pressure source in response to the target reduced pressure exceeding the actual reduced pressure. In this embodiment, the process may emit a signal using an indicator in response to the actual reduced pressure at the tissue site being nonresponsive to increasing the generated reduced pressure.

In one example, the actual reduced pressure at the tissue site is nonresponsive to increasing the generated reduced pressure when the actual reduced pressure at the tissue site fails to increase within a predefined time period in response to increasing the generated reduced pressure. In another example, the actual reduced pressure at the tissue site is nonresponsive to increasing the generated reduced pressure when the actual reduced pressure at the tissue site fails to meet a target reduced pressure within a predefined time period in response to increasing the generated reduced pressure. In a specific non-limiting example, the predefined time period may be in a range of 4 to 6 seconds.

1. Description of the Reduced Pressure Treatment System.

Turning now to FIG. 1, a block diagram of an apparatus for managing reduced pressure delivered to a tissue site is depicted in accordance with an illustrative embodiment of the present invention. Specifically, FIG. 1 shows reduced pressure treatment system 100 for managing the reduced pressure to tissue site 105. Reduced pressure treatment system 100 may be used to apply reduced pressure treatment to tissue site 105. Tissue site 105 may be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 may include a wound, diseased tissue, or defective tissue, the tissue site may further include healthy tissue that is not wounded, diseased, or defective. The application of reduced pressure to tissue site 105 may be used to promote the drainage of exudate and other liquids from tissue site 105, as well as promote the growth of additional tissue. In the case in which tissue site 105 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

The reduced pressure that is applied to tissue site 105 is generated by reduced pressure source 110. Reduced pressure source 110 may be any type of manually, mechanically, or electrically operated pump. Non-limiting examples of reduced pressure source 110 include devices that are driven by stored energy, and which are capable of producing a reduced pressure. Examples of these stored energy, reduced pressure sources include, without limitation, pumps driven by piezo electric energy, spring energy, solar energy, kinetic energy, energy stored in capacitors, combustion, and energy developed by Sterling or similar cycles. Still other devices and processes that may be used or included in reduced pressure source 110 include syringes, lead screws, ratchets, clockwork-driven devices, pendulum-driven devices, manual generators, osmotic processes, thermal heating processes, and processes in which vacuum pressures are generated by condensation. In another embodiment, reduced pressure source 110 may include a pump 112 that is driven by a motor 114 wherein the motor is a direct-current motor powered by a battery (not shown). Preferably, the pump 112 uses low amounts of power and is capable of operating for an extended period of time on a single charge of the battery.

Reduced pressure source 110 provides reduced pressure to the tissue site 105 via dressing 115. Dressing 115 includes manifold 120, which may be placed adjacent to or in contact with tissue 105. Manifold 120 may be a biocompatible, porous material that is capable of being placed in contact with tissue site 105 and distributing reduced pressure to the tissue site 105. Manifold 120 may be made from foam, gauze, felted mat, or any other material suited to a particular biological application. Manifold 120 may include a plurality of flow channels or pathways to facilitate distribution of reduced pressure or fluids to or from tissue site 105.

In one embodiment, manifold 120 is a porous foam and includes a plurality of interconnected cells or pores that act as flow channels. The porous foam may be a polyurethane, open-cell, reticulated foam such as GranuFoam manufactured by Kinetic Concepts, Inc. of San Antonio, Tex. If an open-cell foam is used, the porosity may vary, but is preferably about 400 to 600 microns. The flow channels allow fluid communication throughout the portion of manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through manifold 120. The manifold 120 may further include portions that include "closed cells," These closed-cells portions of manifold 120 contain a plurality of cells, the majority of which are not fluidly connected to adjacent cells. Closed-cell portions may be selectively disposed in manifold 120 to prevent transmission of fluids through perimeter surfaces of manifold 120.

Manifold 120 may also be constructed from bioresorbable materials that do not have to be removed from a patient's body following use of reduced pressure treatment system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 120 may further serve as a scaffold for new cell-growth, or a scaffold material may be used in conjunction with manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-friction (i.e., a high content of air).

The dressing 115 also includes sealing member 125. Manifold 120 may be secured to tissue site 105 using sealing member 125. Sealing member 125 may be a cover that is used to secure manifold 120 at tissue site 105. While sealing member 125 may be impermeable or semi-permeable, in one example sealing member 125 is capable of maintaining a reduced pressure at tissue site 105 after installation of the sealing member 125 over manifold 120. Sealing member 125 may be a flexible drape or film made from a silicone based compound, acrylic, hydrogel or hydrogel-foaming material, or any other biocompatible material that includes the impermeability or permeability characteristics desired for tissue site 105. Sealing member 125 may be formed of a hydrophobic material to prevent moisture absorption by the sealing member 125. In one embodiment, sealing member 125 is configured to provide a sealed connection with the tissue surrounding manifold 120 and tissue site 105. The sealed connection may be provided by an adhesive positioned along a perimeter of sealing member 125 or on any portion of sealing member 125 to secure sealing member 125 to manifold 120 or the tissue surrounding tissue site 105. The adhesive may be pre-positioned on sealing member 125 or may be sprayed or otherwise applied to sealing member 125 immediately prior to installing sealing member 125.

The reduced pressure generated by reduced pressure source 110 may be applied to tissue site 105 using source tube 130 and delivery tube 135. Source tube 130 and delivery tube 135 may be any tube through which a gas, liquid, gel, or other fluid may flow. For example, exudate from tissue site 105 may flow through delivery tube 135. In FIG. 1, source line 130 couples reduced pressure source 110 to canister 140 and delivery tube 135 couples canister 140 to dressing 115. However, in another embodiment, reduced pressure source 135 may be directly coupled to dressing 115 using delivery tube 135.

Source tube 130 and delivery tube 135 may be made from any material. Source tube 130 and delivery tube 135 may be either flexible or inflexible. Also, source tube 130 and delivery tube 135 may include one or more paths or lumens through which fluid may flow. For example, delivery tube 135 may include two lumens. In this example, one lumen may be used for the passage of exudate from tissue site 105 to canister 140. The other lumen may be used to deliver fluids, such as air, antibacterial agents, antiviral agents, cell-growth promotion agents, irrigation fluids, or other chemically active agents, to tissue site 105. The fluid source from which these fluids originate is not shown in FIG. 1. Additional details regarding the inclusion of multi-lumen tubes in reduced pressure treatment system 100 are provided below.

In one embodiment, delivery tube 135 is coupled to manifold 120 via connection member 145. Connection member 145 permits the passage of fluid from manifold 120 to delivery tube 135, and vice versa. For example, exudates collected from tissue site 105 using manifold 120 may enter delivery tube 135 via connection member 145. In another embodiment, reduced pressure treatment system 100 does not include connection member 145. In this embodiment, delivery tube 135 may be inserted directly into sealing member 125 or manifold 120 such that an end of delivery tube 135 is adjacent to or in contact with manifold 120.

Reduced pressure treatment system 100 includes canister 140. Liquid, such as exudate, from tissue site 105 may flow through delivery tube 135 into canister 140. Canister 115 may be any device or cavity capable of containing a fluid, such as gases and liquids, as well as fluids that contain solids. For example, canister 115 may contain exudates from tissue site 105. Source tube 130 and delivery tube 135 may be directly connected to canister 140, or may be coupled to canister 140 via a connector, such as connector 150. The canister 140 may be a flexible or rigid canister, a bag, or pouch fluidly connected to manifold 120 by delivery tube 135. Canister 140 may be a separate canister or may be operably combined with reduced pressure source 110 to collect exudate and fluids.

Reduced pressure treatment system 100 includes pressure sensor 155. Pressure sensor 155 detects an actual reduced pressure at tissue site 105, i.e., the applied pressure. In one non-limiting example, pressure sensor 155 is a silicon piezoresistive gauge pressure sensor. The pressure sensor 155 is the only pressure sensor included in reduced pressure treatment system 100, no other pressure sensor other than pressure sensor 155 is included. Pressure sensor 155 detects the applied pressure at tissue site 105 via control tube 160. Control tube 160 is any tube through which a gas may flow. Control tube 160 may be made from any material. Control tube 160 may be either flexible or inflexible. Also, control tube 160 may include one or more paths or lumens through which fluid may flow.

In FIG. 1, control tube 160 is shown as passing through connector 150. However, the placement of control tube 160 may be varied to accommodate particular needs and applications. For example, control tube 160 may be routed through canister 140, along an outside surface of canister 140, or may bypass canister 140. The end of control tube 160 that is opposite of pressure sensor 155 may be coupled to manifold 120 via connector 145. In another example, control tube 160 may be inserted directly into sealing member 125 or manifold 120 such that an end of control tube 160 is adjacent to or in contact with manifold 120.

Figure 2:
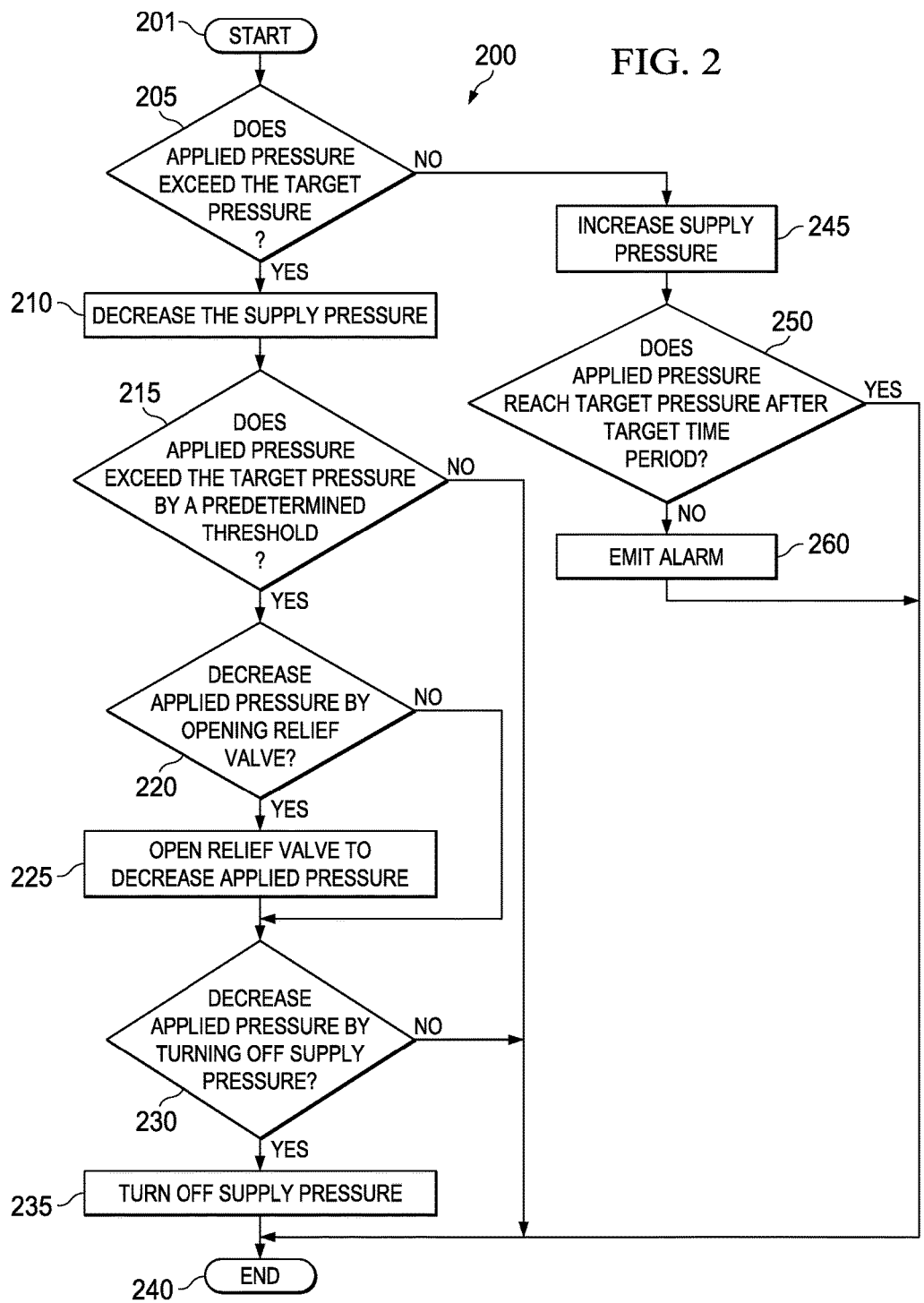
FIG. 2 is a flowchart illustrating a process for managing reduced pressure at a tissue site in accordance with an illustrative embodiment of the invention.

In another embodiment, delivery tube 135 and control tube 160 are each lumens in a single multi-lumen tube. Source tube 130 and control tube 160 may also each be lumens in a single multi-lumen tube. In the example in which reduced pressure source 110 is coupled to manifold 120 using only delivery tube 135, a single multi-lumen tube may be used to couple both reduced pressure source 110 and pressure sensor 155 to manifold 120. Turning to FIG. 2, a perspective view of a multi-lumen tube is depicted in accordance with an illustrative embodiment of the present invention. Specifically, FIG. 1A depicts multi-lumen tube 190, which may be implemented in a reduced pressure treatment system, such as reduced pressure treatment system 100 in FIG. 1.

Multi-lumen tube 190 includes two lumens. Specifically, multi-lumen tube 190 includes lumens 192 and 194. Although multi-lumen tube 190 includes two lumens 192 and 194, multi-lumen tube may have any number of lumens, such as three, four, or ten. In one embodiment, one of lumens 192 and 194, such as lumen 192, is a delivery tube or source tube, such as delivery tube 135 and source tube 130 in FIG. 1. In another embodiment, one of lumens 192 and 194, such as lumen 194, is a control tube, such as control tube 160 in FIG. 1. By incorporating a combination of a delivery tube, source tube, and control tube as lumens in a single multi-lumen tube, the number of separate tubes included in the reduced pressure treatment system may be reduced. The reduced number of tubes simplifies the reduced pressure treatment system for use by a user, and lessens the burden of carrying the reduced pressure treatment system.

Pressure sensor 155 may be located anywhere on reduced pressure treatment system 100. Referring back to FIG. 1, pressure sensor 155 is shown to be remote from tissue site 105. In this example, the reduced pressure at tissue site 105 may be detected from remotely located pressure sensor 155 through control tube 160, which permits the flow of gas. Also in this example, pressure sensor may be directly or indirectly coupled to other remotely located components of reduced pressure treatment system 100, such as reduced pressure source 110, canister 140, or any other illustrated component of reduced pressure treatment system 100. In another example, pressure sensor 155 may not require the use of control tube 160 to detect the pressure at tissue site 105. In one non-limiting example, pressure sensor 155 is directly coupled to manifold 120 or placed between sealing member 125 and manifold 120.

2. Controlling the Reduced Pressure.

Reduced pressure treatment system 100 includes control tube valve 165. Control tube valve 165 may be coupled to control tube 160. Control tube valve 165 may be any valve capable of relieving the reduced pressure in control tube 160. Non-limiting examples of control tube valve 165 include a pneumatic solenoid valve, a proportional valve, or a mechanical valve. In one example, control tube valve 165 may be manually controlled by a human being. In another example, control tube valve 165 may be controlled by controller 170. In one embodiment, control tube valve 165 may be opened to relieve the reduced pressure in control tube 160 when a blockage is detected in control tube 160. Such a blockage may occur, for example, when exudate or other fluid from tissue site 105 clogs control tube 160. By relieving the reduced pressure in control tube 160 via control tube valve 165, the blockage may be cleared from control tube 160.

Reduced pressure treatment system 100 also includes relief valve 175. Relief valve 175 may be a valve that is coupled to any one of or any combination of source tube 130, canister 140, connector 150, delivery tube 135, connector 145, reduced pressure source 110, or dressing 115. Relief valve 175 may any type of valve capable of relieving the reduced pressure at tissue site 105. Non-limiting examples of relief valve 175 include a pneumatic solenoid valve, a proportional valve, or a mechanical valve. In one example, relief valve 175 may be opened to relieve the reduced pressure at tissue site 105. Relief valve 175 may also be used to manage the reduced pressure at tissue site 105. Additional details regarding the use of relief valve 175 and other components of the reduced pressure treatment system 100 to manage the reduced pressure at tissue site 105 are provided below.

Reduced pressure treatment system includes controller 170. Controller 170 is any device capable of processing data, such as data from pressure sensor 155. Controller 170 may also control the operation of one or more components of reduced pressure treatment system 100, such as reduced pressure source 110, relief valve 175, control tube valve 165, pressure sensor 155, or indicator 180. In one embodiment, controller 170 receives and processes data, such as data from pressure sensor 155, and controls the operation of one or more components of reduced pressure treatment system 100 to manage the applied pressure at tissue site 105.

In one embodiment, controller 170 determines a target pressure for tissue site 105. The target reduced pressure may be a user-definable reduced pressure for tissue site 105. The target reduced pressure may also be determined by controller 170. In one example, the target pressure is a reduced pressure that provides an effective treatment of tissue site 105 and takes into account safety issues associated with applying reduced pressure to tissue site 105.

In one example, pressure sensor 155 detects the applied pressure at tissue site 105 and inputs the reduced pressure measurement to the controller 170. The controller 170 may compare the reduced pressure received from pressure sensor 155 with the target pressure to determine the difference in pressure, i.e., the "applied pressure differential" between them. Controller 170 may then perform or direct a component of reduced pressure treatment system 100 to perform a reduced pressure management function based on the applied differential pressure. In one embodiment, controller 170, in performing the reduced pressure management function based on the applied differential pressure, decreases the reduced pressure generated by reduced pressure source 110, i.e., the supply pressure, in response to the applied pressure exceeding the target pressure or by exceeding a maximum value for the applied differential pressure.

For example, if reduced pressure source 110 is a motorized or otherwise electrically operated reduced pressure source, such as direct-current motor 114, the motor or electrical process may be slowed such that reduced pressure source 110 generates a decreased amount of supply pressure. In another embodiment, controller 170 simply turns off or shuts down reduced pressure source 110 in response to the applied pressure measured by pressure sensor 155. In another embodiment, controller 170 opens relief valve 175 to decrease the applied pressure at tissue site 105 in response to the reduced pressure measured by pressure sensor 155. The maximum value of the applied differential pressure may be set by a user or by a component of reduced pressure treatment system 100 such as controller 170. In one example, the maximum value of the applied differential pressure is a threshold that helps to ensure the safety of tissue at tissue site 105. Thus, this embodiment may be implemented as a safety mechanism using the single pressure sensor 155.

In another example, controller 170, in performing the reduced pressure management function based on the applied pressure differential, increases the supply pressure generated by reduced pressure source 110. For example, if reduced pressure source 110 is a motorized or otherwise electrically operated reduced pressure source, such as motor 114, the pace of the motor or electrical process may be increased such that reduced pressure source 110 generates an increased amount of supply pressure. In another embodiment, controller 170 determines a responsiveness of the applied pressure at tissue site 105, as measured by pressure sensor 155, to an increase in the supply pressure generated from reduced pressure source 110. In one example, controller 170 may detect when the supply pressure is increased or decreased. For example, controller 170 may be able to detect when the motor speed or compression speed of reduced pressure source 110 has increased or decreased. Other parameters that may be detected by controller 170 to determine such an increase or decrease include the current draw of a motor, which may indicate the pump's speed. Controller 170 may also be able to infer that the supply pressure generated by reduced pressure source is increased or decreased based on the comparison between the applied pressure measured by pressure sensor 155 and the target pressure.

In one embodiment, controller 170 inputs indicator 180 to emit a signal in response to the applied pressure at tissue site 105, as measured by pressure sensor 155, being nonresponsive to increasing the supply pressure. In one embodiment, indicator 180 is a light emitting diode, or "LED." In this embodiment, indicator 180 illuminates in response to the applied pressure at tissue site 105 being nonresponsive to increasing the supply pressure. In another embodiment, indicator 180 is a sound emitting device, such as a speaker. In this embodiment, indicator 180 emits a sound in response to the applied pressure at tissue site 105 being nonresponsive to increasing the supply pressure.

In some cases, the applied pressure at tissue site 105 is nonresponsive to increasing the supply pressure when the applied pressure at tissue site 105 fails to increase within a predefined time period in response to increasing the supply pressure. Such nonresponsiveness may indicate that one or more components of reduced pressured treatment system 100, such as delivery tube 135 or source tube 130, are blocked or have a leak. For example, liquid, such as exudate, from tissue site 105 may have clogged delivery tube 135 or source tube 130. In another example, a rupture may have occurred at a location along delivery tube 135 or source tube 130. The predefined time period may be any time period, and may be set by a user of reduced pressure treatment system 100, or a component of reduced pressure treatment system 100, such as controller 170. In one example, the predefined time period in a range of one second to ten seconds or four seconds to six seconds. In one specific non-limiting example, the predefined time period is five seconds.

In another embodiment, the applied pressure at tissue site 105 is nonresponsive to increasing the supply pressure when the applied pressure at tissue site 105 fails to meet the target pressure within a predefined time period in response to increasing the supply pressure. Similar to the previously described embodiment, such nonresponsiveness may indicate that one or more components of reduced pressured treatment system 100, such as delivery tube 135 or source tube 130, are blocked or have a leak.

In another embodiment of the present invention, if reduced pressure source 110 is vacuum pump 112 and motor 114, a sensor may be coupled to the vacuum pump 112 or motor 114 to measure the pump or motor speed. The measurements acquired by the sensor may be used to infer the supply pressure delivered by the pump, thereby providing a mechanism for determining whether leaks or blockages are present and distinguishing between them. For example, detection of leaks may be performed by monitoring the speed of either or both of the pump 112 or motor 114. If a leak occurs while reduced pressure treatment is being administered, either or both of the pump speed or motor speed will likely increase indicating that the pump is generating more supply pressure. If a blockage occurs, the speed of either or both of the pump or motor will likely decrease. The output from the pump or motor speed sensor may be used by controller 170 to emit a signal using indicator 180 during a leak or blockage condition.

In one specific illustrative example, reduced pressure source 110 includes a motor and a sensor for detecting the speed of the motor. Indicator 180 may emit a signal when the speed of the motor changes by a threshold amount. The threshold amount may be any amount, and may be set by a user of reduced pressure treatment system 100, or a component of reduced pressure treatment system 100, such as controller 170. The threshold amount may be expressed in terms of a finite quantity, a percentage, or any combination thereof.

Turning now to FIG. 2, a flowchart 200 illustrating a process for managing reduced pressure at a tissue site is depicted in accordance with an illustrative embodiment of the present invention. The process illustrated in FIG. 2 may be implemented by a controller, such as controller 170 in FIG. 1, in conjunction with other components of a reduced pressure treatment system, such as components of reduced pressure treatment system 100 in FIG. 1. The process starts (step 201) by determining a target pressure and detecting an applied pressure at a tissue site using a single pressure sensor. The process compares the applied pressure to the target pressure and provides a comparison signal to perform a reduced pressure management function based on the comparison signal as illustrated in the remaining portions of the flowchart 200.

The process proceeds by determining whether the applied pressure exceeds the target pressure (step 205). If the process determines that the applied pressure does not exceed the target pressure, the process increases the supply pressure (step 245). The process proceeds by determining whether the applied pressure reaches the target pressure after a target time period (250). If the applied pressure has reached the target pressure, the process is then terminated. However, if the process has determined the applied pressure has not yet reached the target pressure after the predetermined target time period, the process causes an alarm to be emitted (step 260) which again terminates the process providing an indication to a user that a leak may have occurred in the system. Returning to step 205, if the process determines the applied pressure exceeds the target pressure, the process decreases the supply pressure that is generated by the reduced pressure source (step 210).

The process next determines whether the applied pressure exceeds the target pressure by a predetermined maximum threshold (step 215). If the process determines that the applied pressure does not exceed the target pressure by the predetermined maximum threshold, the process terminates. Returning to step 215, if the process determines that the applied pressure exceeds the target pressure by the predetermined maximum threshold, the process determines whether to decrease the applied pressure by opening a relief valve (step 220). If the process determines to decrease the applied pressure by opening the relief valve, the process opens the relief valve to decrease the applied pressure at the tissue site (step 225). Returning to step 220, if the process determines not to decrease the applied pressure by opening a relief valve, the process determines whether to decrease the applied pressure by turning off the supply pressure (step 230). If the process determines to decrease the applied pressure by turning off the supply pressure, the process turns off the supply pressure source (step 235) and then terminating. Returning to step 230, if the process determines not to decrease the applied pressure by turning off the applied pressure source, the process terminates.

3. Motor-Drive System for a DC Motor.

Figure 3:
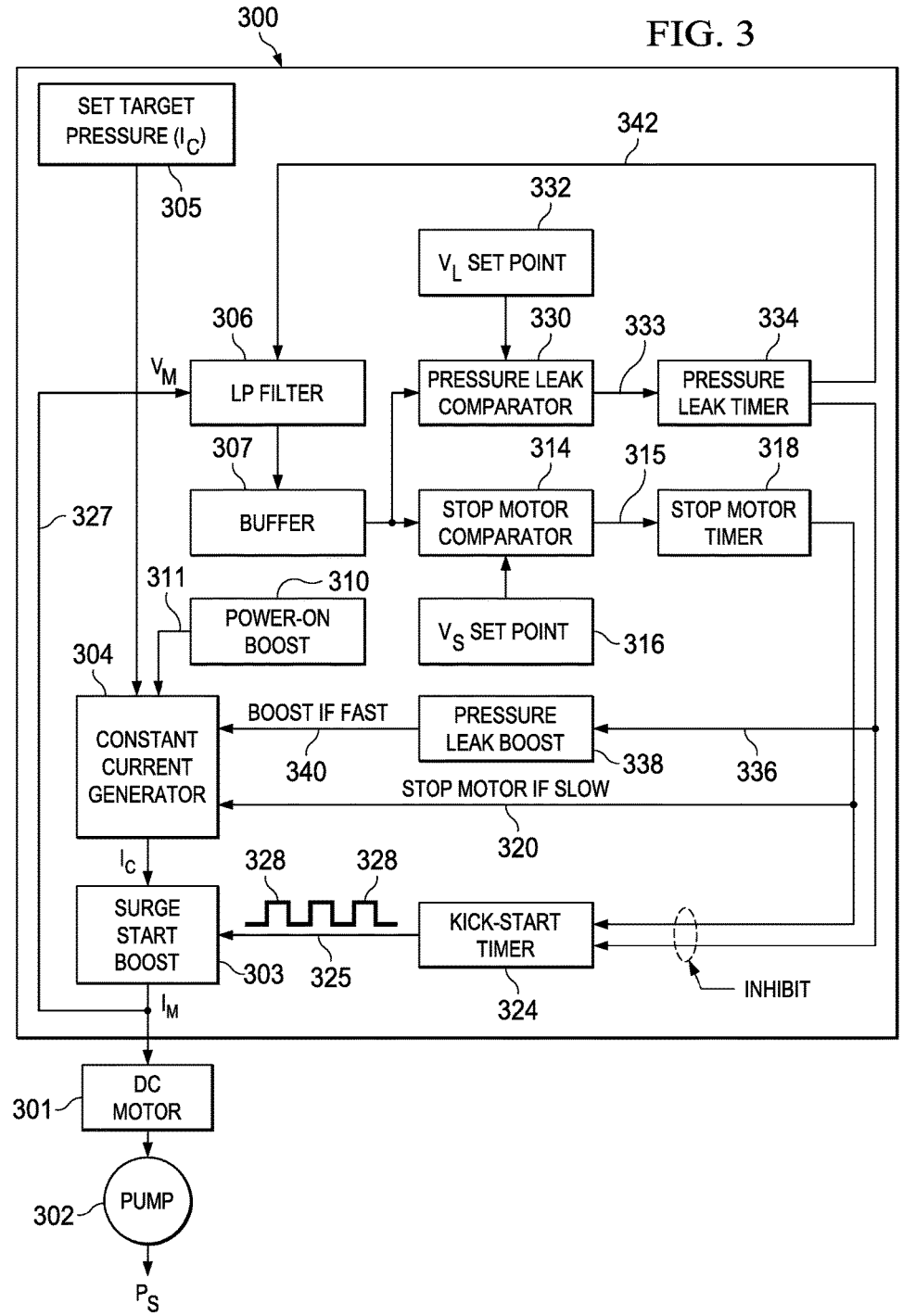
FIG. 3 is a detailed block diagram of a first motor-drive system for providing a constant current to a DC motor that drives a pump in accordance with an illustrative embodiment of the present invention.
Figure 4:
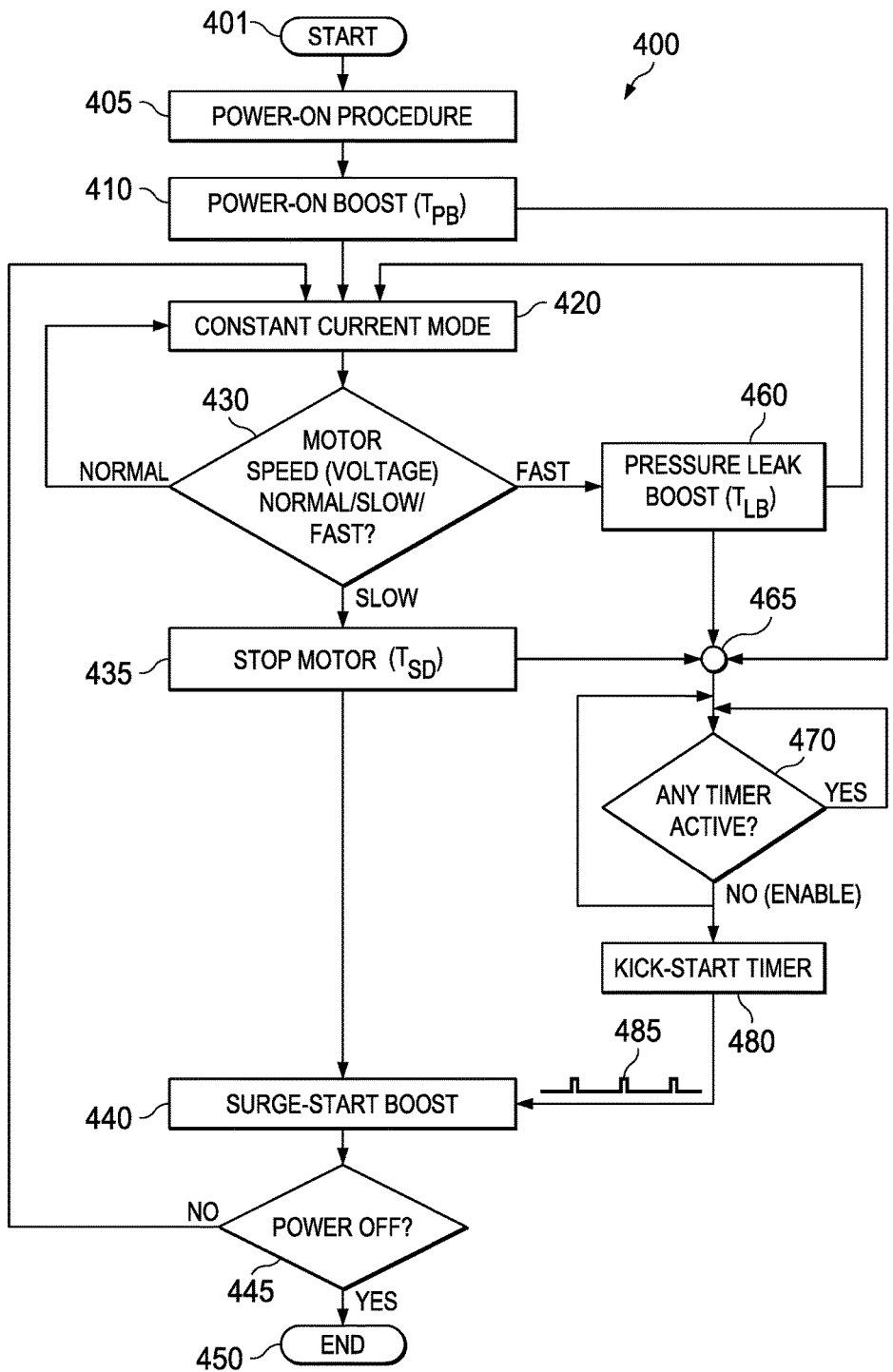
FIG. 4 is a circuit logic diagram illustrating a process for controlling a DC motor that drives a pump for generating a reduced pressure in accordance with an illustrative embodiment of the invention.

In another embodiment of the present invention, the motor 114 may be a DC-driven motor and the pump 112 may be a diaphragm type mechanically driven by the DC-driven motor. Referring more specifically to FIGS. 3 to 5, the controller 170 may include a motor-drive system 300 that provides a constant current $I_C$ to DC-driven motor which is preferably a brushed DC motor 301 having a rated voltage $V_R$ sufficiently high to drive a diaphragm pump 302. The motor-drive system 300 controls the current drawn by the DC motor 301 ($I_M$) to maintain the motor current $I_M$ at the constant current $I_C$ level. The constant current $I_C$ is selected to achieve a motor speed that causes the diaphragm pump 302 to generate a supply pressure $P_S$ in the proximity of a target pressure $P_T$ that is selected by a user as the desired pressure therapy. In one exemplary embodiment, the DC motor 301 has a rated voltage $V_R$ of about 4.5 volts with constant current $I_C$ being said at approximately 67 milliamps so that the diaphragm pump 302 generates a supply pressure $P_S$ at approximately 125 mmHg.

The motor-drive system 300 may be incorporated into the controller 170 which may continue to function as described above or may be structured as a discrete component of the reduced pressure treatment system 100. The motor-drive system 300 may operate in conjunction with or in lieu of the pressure sensor 155 that senses the applied pressure at the tissue site 105, and may utilize either single or multi-lumen conduits depending on the specific application. The pressure sensor 155 provides an input to the controller 170 for providing a direct measurement of the pressure being applied at the tissue site 105 that may be different from the supply pressure $P_S$ generated by the pump 302.

In a constant current mode when the constant current $I_C$ is applied to the DC motor 301, the DC motor 301 begins by racing at a high speed to increase the supply pressure $P_S$ from ambient to the target pressure $P_T$. Initially, the voltage drop across the motor ($V_M$) spikes to the rated voltage $V_R$ of the DC motor 301 and then decreases proportionally with the speed of the DC motor 301 as it slows down in response to the increasing supply pressure $P_S$. When the supply pressure $P_S$ reaches the target pressure $P_T$, the DC motor 301 slows down to the point of stalling with the motor voltage $V_M$ dropping proportionally to a very low value. A stall voltage ($V_S$) is selected as the nominal voltage level below which the motor voltage $V_M$ must not fall before providing a signal indicating that the supply pressure $P_S$ has probably reached the target pressure $P_T$ and that the DC motor 301 should be stopped. The motor-drive system 300 measures the motor voltage $V_M$, compares the motor voltage $V_M$ to the stall voltage $V_S$, and cuts off the current to the DC motor 301 when the motor voltage $V_M$ falls below the stall voltage $V_S$. Essentially, when the motor voltage $V_M$ falls below the stall voltage $V_S$, the motor-drive system 300 is providing an indirect indication that the supply pressure $P_S$ has reached the target pressure $P_T$ without using a pressure sensor to directly measure the supply pressure $P_S$.

DC motors typically run using a constant voltage wherein the motor current drops as the rotational speed of the DC motor increases. When a load is applied to the DC motor that slows down the rotor of the DC motor, the current drawn through the motor, i.e., the motor current ($I_M$), increases which increases the power demanded at such reduced speeds. A constant current motor drive in a reduced pressure system offers at least two advantages over a constant voltage motor drive. Firstly, when the DC motor slows down in a constant voltage system as the supply pressure $P_S$ approaches the target pressure $P_T$, the increasing pressure load causes the DC motor to draw more current. Because both the motor current and the motor voltage are high, the DC motor requires more power for extended periods of time during which the pump is generating a supply pressure $P_S$ in the proximity of the target pressure $P_T$. When the DC motor 301 slows down in a constant current system as described above, the motor voltage $V_M$ decreases so that the power demanded drops as well to a level below the power demands of a constant voltage drive system.

Secondly, when the motor voltage $V_M$ drops below the stall voltage $V_S$, the DC motor 301 can be turned off assuming that the supply pressure $P_S$ is proximate to the desired target pressure $P_T$ as described above. Consequently, power consumption is further reduced. More importantly, the supply pressure $P_S$ is controlled without the need for a separate pressure sensor that would provide a direct measurement of the supply pressure $P_S$ or the need for the negative feedback circuitry required by a system using a pressure sensor. As indicated above, the elimination of a pressure sensor for measuring the supply pressure $P_S$ greatly reduces the cost and a potential source of contamination. Thus, the motor-drive system 300 provides a constant current $I_C$ to the DC motor 301 and monitors the voltage differential between the motor voltage $V_M$ and the stall voltage $V_S$ for inferentially controlling the supply pressure $P_S$ provided by the pump 302 without an additional pressure sensor or any feedback circuitry required for a system using a pressure sensor.

The motor-drive system 300 includes a constant current generator 304 for providing the constant current $I_C$ as the motor current ($I_M$) to the DC motor 301 via a surge-start power boost circuit, i.e., the surge-boost module 303. The surge-boost module 303 simply ensures that the DC motor 301 reliably starts when a low level of power is reapplied to the DC motor 301 after stopping for any reason. The target pressure $P_T$ is set by set target pressure module 305 that provides a signal to the constant current generator 304 for setting a constant current $I_C$ that achieves the desired target pressure $P_T$. The target pressure module 305 includes an input device that can be adjusted by the manufacturer or in some cases a user of the reduced pressure treatment system 100 to vary the constant current $I_C$ for adjusting the target pressure $P_T$ within a range for the pressure therapy that is desired, e.g., 120-150 mmHg. The motor voltage $V_M$ across the DC motor 301, i.e., the raw motor voltage, $V_M$ (raw), is filtered by a low-pass filter 306 and buffered by buffer module 307 to smooth out any fluctuations. The filtered motor voltage, $V_{MF}$ may be applied to a differential amplifier (not shown) to provide a ground-reference signal for other components of the motor drive system 300 such as the comparators.

The motor-drive system 300 may include several modes of operation such as, for example, a "power-on boost" mode. In this start-up mode, more power is applied to the DC motor 301 for a set period of time, i.e., the power-on boost period ($T_{PB}$), after starting the DC motor 301 to achieve a more rapid pull-down of the supply pressure $P_S$, i.e., a higher negative pressure. Fundamentally, the full-rated voltage may be applied to the DC motor 301 to more rapidly increase the speed of the DC motor 301 so that the desired supply pressure $P_S$ is more quickly achieved. For example, the motor voltage $V_M$ may be increased to about 4.5 volts which falls to an operational voltage of about 1.5 volts after the power-on boost period $T_{PB}$ when the supply pressure $P_S$ approaches the target pressure $P_T$ as indicated by the rising portion of pressure curve $P_S(1)$. Under a normal constant-current condition, the supply pressure $P_S$ increases to a target pressure $P_T$, e.g., 145 mmHg, in due course as indicated by the rising portion of the pressure curve $P_S(I_C)$; increasing the motor voltage $V_M$ simply draws down the supply pressure $P_S$ faster.

The power-on boost mode includes a power-on boost module 310 that provides a power-boost signal 311 to the constant current generator 304 to increase the motor voltage $V_M$ applied to the DC motor 301. The higher motor voltage $V_M$ increases the rotational speed of the DC motor 301 so that the supply pressure $P_S$ reaches the target pressure $P_T$ more quickly. It should be understood that the power-on boost feature takes the motor-drive system 300 out of a constant-current condition for this short period of time ($T_{PB}$) because the motor voltage $V_M$ is increased to apply more power to the DC motor 301 in order to more rapidly increase the supply pressure $P_S$. The power-on boost mode is typically utilized at the commencement of the wound therapy treatment, but may also be utilized at other times such as, for example, after a caregiver changes the dressing 115.

Figure 5B:
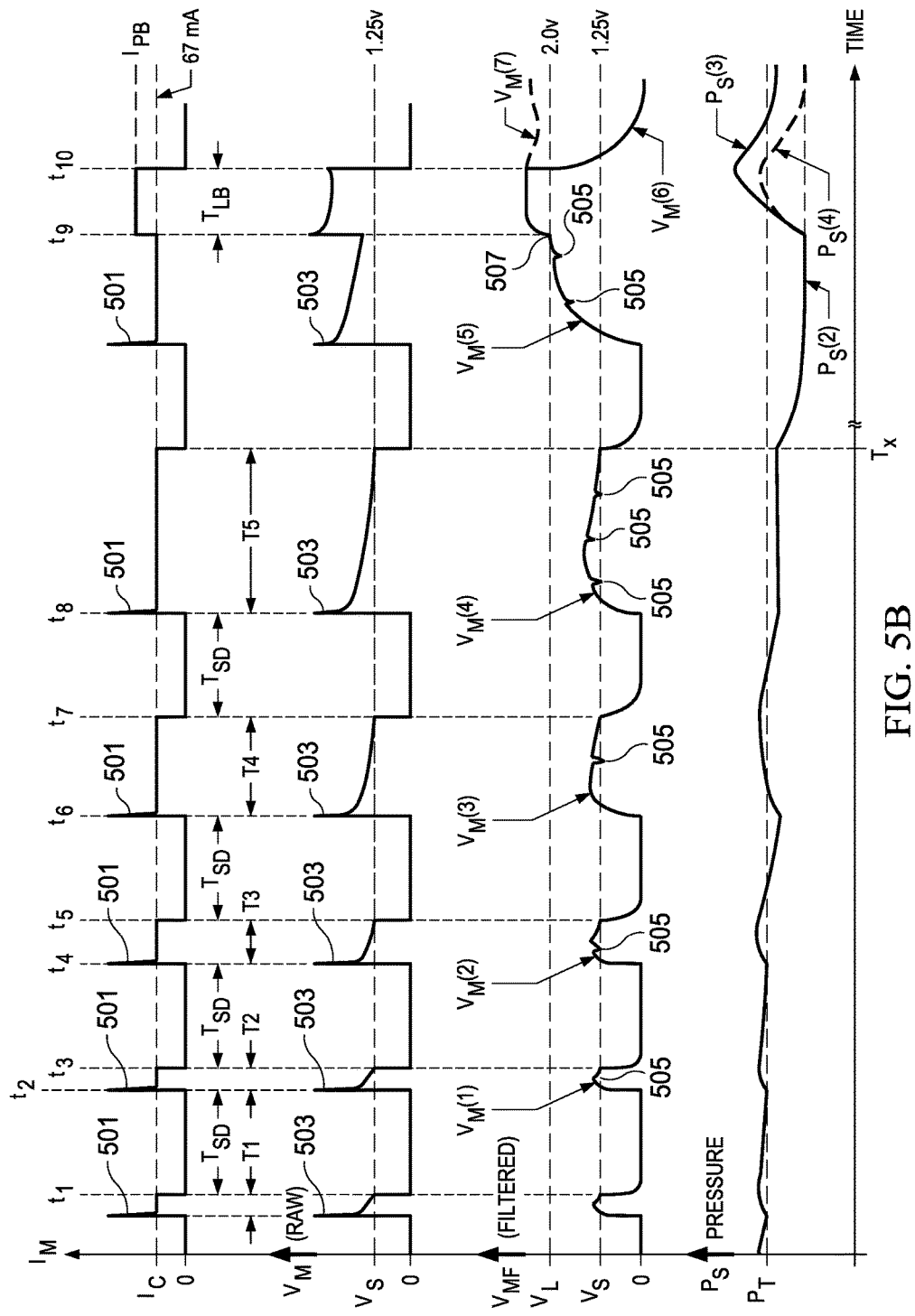
FIG. 5B is a graph illustrating circuit waveforms for the motor current and voltages corresponding to the pressure generated over the time period indicated in FIG. 5A.

Referring more specifically to FIG. 5B which is an illustration of the motor current $I_C$, the raw motor voltage $V_M$ (raw), and the filtered motor voltage $\backslash T_{NT}$ associated with the supply pressure $P_S$ over the short period of time ($T_X$) shown in FIG. 5A. After the power-on boost period ($T_{PB}$) on start-up times out, the motor-drive system 300 returns to the constant-current condition where the motor current $I_M$ is about equal to the constant current $I_C$ setting as shown in FIG. 5B. The motor-drive system 300 remains in the constant current condition for a variable period of time ($T_{ON}$) depending on how long it takes the supply pressure $P_S$ to reach the target pressure $P_T$. As the dressing 115 develops more leaks over time, for example, the motor-drive system 300 works harder to combat the leaks so that the time-on periods $T_{ON}$ last longer as illustrated by the time-on periods T1, T2, T3, and T4 where the time-on period T4 is longer than the time-on period T1.

When the supply pressure $P_S$ reaches the target pressure $P_T$, the motor-drive system 300 is further configured to operate in a mode of operation wherein the DC motor 301 is stopped if the rotational speed is too slow, i.e., the "stop-motor-if-slow" mode. Essentially, the motor-drive system 300 includes circuitry that shuts down the pump 301 for a set period of time. After the shut-down period ($T_{SD}$), the filtered motor voltage $V_{MF}$ drops below the stall voltage $V_S$ at turn-off time $t_1$ as described above and shown in FIG.

5B. The buffer 307 provides the buffered and filtered motor voltage $V_{MF}$ to a stop-motor or stall comparator 314 that compares the filtered motor voltage $V_{MF}$ to the stall voltage $V_S$. The manufacturer or user sets the stall voltage $V_S$ utilizing set point module 316 that provides the desired stall voltage $V_S$ to the stall comparator 314.

The stall comparator 314 provides a stall condition signal 315 to a stop-motor or stall timer 318 when the motor voltage $V_M$ drops below the stall voltage $V_S$ that triggers the stall timer 318 to run for a fixed period of time, i.e., the shut-down period ($T_{SD}$). When the stall timer 318 is set to count down the shut-down period $T_{SD}$, it provides a stop signal 320 to the constant current generator 304 to reduce the motor current ($I_M$) to zero as indicated, for example, by the off-times ($t_{off}$) at $t_1$, $t_3$, $t_5$, and $t_7$ marking the end of the respective time-on periods (T1-T4). After the shut-down period ($T_{SD}$) expires, the stop signal 320 is removed so that the constant current generator 304 triggers the surge-start boost 303 to reconnect the DC motor 301 to the current source at on-times ($t_{on}$) $t_2$, $t_4$, $t_6$, and $t_8$ causing a spike in the motor current $T_M$ and the raw motor voltage $V_M$ (raw), but not in the filtered motor voltage $V_{MF}$ as described above.

For example, the stall voltage $V_S$ may be set at a value of about 1.25 volts so that the stall comparator 314 provides a stall condition signal to the stall timer 318 when the filtered motor voltage $V_{MF}$ drops below the stall voltage $V_S$ at off-times ($t_{off}$) $t_1$, $t_3$, $t_5$, and $t_7$ as shown in FIG. 5 11. The stall timer 318 provides a stop signal 320 each time, and each time shuts down the DC motor 301 such that the motor voltage $V_M$ drops to zero for the shut-down period $T_{50}$ in the stop-motor-if-slow mode. After the shut-down time period ($T_{SD}$) expires, the DC motor 301 restarts at a low power level and the filtered motor voltage $V_M$ (filter) ramps up at on-times ($t_{on}$) $t_2$, $t_4$, $t_6$, and $t_8$ to an operational voltage greater than the stall voltage $V_S$ which may be a value of about 1.5 volts, as indicated by $V_M(1)$, $V_M(2)$, $V_M(3)$, and $V_M(4)$. Thus, a complete operational cycle for the DC motor 301 includes the variable time-on periods $T_{ON}$ (T1, T2, T3, and T4) during the constant-current modes and the constant shut-down time periods $T_{SD}$ as shown in FIG. 5B.

The motor-drive system 300 also includes a kick-start mode of operation to ensure that the pump 301 does not stop for too long at any time during the operational cycle of the DC motor 301 as long as the motor-drive system 300 is not in the power-on boost mode or the stop-motor-if-slow mode. Both the power-on boost signal 311 and the stop signal 320 may also be applied to the inhibit input (I) of a kick-start timer 324 that provides a kick-start timing signal 325 to the surge-start boost module 303 causing it to operate as described above. The kick-start timing signal 325 may be an asynchronous pulse signal that provides successive pulses 328 when not inhibited by any of the other operational modes at fixed frequency or time period ($T_{KS}$). Each pulse 328 triggers the surge-start boost module 303 to briefly stop and restart the DC motor 301 in a low-power, restart mode. Because the kick-start timer 324 is not needed when the DC motor 301 is running fast in the power-on boost mode or stopped, the power-on boost signal 311 and the stop signal 320 inhibit the kick-start timer 324 to disable the surge-start boost module 303 for their respective time periods.

After the shut-down period $T_{SD}$ and the power-on boost period $T_{PB}$ expire, the stop signal 320 and the power-on boost signal 311 no longer inhibit the kick-start timing signal 325 so that the surge-start boost module 303 can be triggered by the pulses 328 of the kick-start timing signal 325 as illustrated by the small negative spikes 505 that occur in the filtered motor voltage $V_M$ (filter) during the constant current mode of operation to ensure that the constant current generator 304 is providing power to the DC motor 301. Several negative spikes 505 may occur during time-on periods $T_{ON}$ of a constant current mode such as during time-on period T5. The kick-start timer 324 and the surge-start boost module 303 function as a watchdog timer to ensure that the DC motor 301 continues running in the constant-current mode and, as such, they function as a safety feature that is not necessary for the operation of the motor-drive system 300.

Referring again to FIG. 5B for an example, the stop signal 320 occurs at the off-times ($t_{off}$) at $t_1$, $t_3$, $t_5$, and $t_7$ which inhibits the kick-start timing signal 325 so that the surge-start boost module 303 is not triggered to turn over the DC motor 301. When the shut-down time period $T_{50}$ expires at the on-times ($t_{on}$) $t_2$, $t_4$, $t_6$, and $t_8$, the kick-start timing signal 325 is no longer inhibited so that it continues to trigger the surge-start boost module 303 to ensure that the DC motor 301 restarts to maintain the supply pressure $P_S$ in the proximity of the target pressure $P_T$. After the DC motor 301 restarts at a low power level, the filtered motor voltage $V_{MF}$ rises back to an operational speed of about 1.5 volts. The stop-motor mode maintains the supply pressure $P_S$ at or near the target pressure $P_T$ in the absence of significant leakage to compensate for the normal level of operational leakage from the reduced pressure treatment system 100. The kick-start mode ensures that the DC motor 301 continues running when operating at a low power, i.e., fixed current and low voltage.

As indicated above, the stop-motor mode maintains the supply pressure $P_S$ in the proximity of the target pressure $P_T$ in the absence of significant leakage. When the leakage is significant and causes a rapid decrease in the applied pressure at the tissue site 105, the speed of the motor increases in response to the reduced load on the pump 302 as indicated by the filtered motor voltage $V_{MF}$ that rises at the same time as indicated by the motor voltage $V_M(5)$. In one embodiment of the motor-drive system 300, the user selects a ceiling for the motor voltage $V_M$ at a specific value, i.e., a leak voltage ($V_L$). When the filtered motor voltage $V_{MF}$ exceeds the leak voltage ($V_L$) by any significant design margin, a significant leak condition is present in the system. Thus, the motor-drive system 300 also includes a "power-boost-if-fast" mode of operation which includes modules for providing an indication of significant leaks in the system. The buffer 307 also provides the filtered motor voltage $V_{MF}$ to a pressure leak comparator 330. The manufacturer or a user sets the leak voltage $V_L$ at an input device 332 that provides a leak signal reflective of the leak voltage $V_L$ to the leak comparator 330. When the motor voltage $V_M$ is equal to or greater than the leak voltage $V_L$, the leak comparator 330 provides a leak indicator signal 333 to a leak timer 334 which provides a power boost signal 336 to a pressure leak power boost module 338. The pressure leak power boost module 338 provides a power boost signal 340 to the constant current generator 304 which drives at an increased power level, i.e., the boost leak power.

The boost leak power may be generated by either increasing the current to the DC motor 301 beyond the preset constant current or by again increasing the motor voltage $V_M$ applied to the DC motor 301. The boost leak power generates additional supply pressure $P_S$ to compensate for a significant leak in the reduced pressure treatment system 100. The leak timer 334 times out after a leak boost time period ($T_{LB}$) during which the boost leak power is applied to the DC motor 301. After the leak boost time period $T_{LB}$ expires, the pressure leak timer 334 may provide a discharge signal 342 to the capacitor of the filter 306 to reset the leak comparator 330 so that the boost leak power is no longer applied to the DC motor 301. The DC motor 301 should return to its normal speed as indicated by the operational motor voltage $V_M$ associated with that speed if the significant leak is corrected. The pressure leak timer 334 also provides the power boost signal 336 to the kick-start timer 324 to again inhibit the kick-start timing signal 325 and disable the surge-start boost module 303 as described above when the power boost signal 340 is being applied to the constant current generator 304. After the leak boost time period $T_{LB}$ has expired, the kick-start timing signal 325 is no longer inhibited so that it continues to trigger the surge-start boost module 303 as described above.

Referring again to FIG. 5B for an example of the operation of the power-boost-if-fast mode, the manufacturer or a user may set the leak voltage $V_L$ at a value of 2.0 volts. If a significant leak occurs at time $t_9$, the supply pressure $P_S$ will drop below the target pressure $P_T$ to value such as, for example, $P_S(2)$ which causes the DC motor 301 to run faster. As a result, the filtered motor voltage $V_{MF}$ will also increase and eventually exceed the leak voltage $V_L$ at 507 which causes the leak comparator 330 to trigger the leak timer 334. When the leak timer 334 is triggered, the boost leak power is applied to the constant current generator 304 by increasing, for example, the motor current $I_M$ above the constant current $I_C$ to a value $I_{PB}$ for the leak boost time period ($T_{LB}$). The boost leak power causes the DC motor 301 to run even faster to overcome the loss of supply pressure $P_S$ and increase the supply pressure $P_S$ back up to the target pressure $P_T$ as indicated by supply pressure $P_S(3)$. If the supply pressure $P_S$ remains in the proximity of the target pressure $P_T$, the filtered motor voltage $V_{MF}$ provides an indication that the leak has been overcome because the filtered motor voltage $V_{MF}$ drops below the leak voltage $V_L$ back down below the stall voltage $V_S$ after the leak-boost time period ($T_{LB}$) expires as indicated by motor voltage $V_M(6)$.

Nevertheless, the power-boosted DC motor 301 may not be able to overcome a significant leak that persists and the corresponding loss of supply pressure $P_S$ after the expiration of the leak boost time period ($T_{LB}$). This situation would be indicated if the pressure leak indicator 330 again provides a leak-condition signal 333 because the motor voltage at time $t_{10}$ is still greater than the leak voltage $V_L$ as indicated by motor voltage $V_M(7)$. This inferentially indicates that the supply pressure $P_S$ has not yet reached the target pressure $P_T$, or has reached the target pressure $P_T$ and fallen below the target pressure $P_T$ again, as indicated by supply pressure $P_S(4)$. Consequently, the power boost signal 340 retriggers the constant current generator 304 to provide the boost leak power to the DC motor 301. The leak comparator 330 stops triggering the leak timer 334 only when the filtered motor voltage $V_{MF}$ drops below the leak voltage $V_L$. In some cases, the leak may be bad enough so that the supply pressure $P_S$ cannot compensate for the lost pressure and never reaches the target pressure $P_T$ as indicated by a filtered motor voltage $V_{MF}$ that never drops below the leak voltage $V_L$. In such cases, the pressure sensor 155 may be used to confirm that a significant leak is still present as indicated by the indicator 172. Although the pressure sensor 155 is not necessary for the operation of the invention, it can provide some backup to ensure the system is properly operating.

Thus, the DC motor 301 normally operates at a speed sufficient to maintain the target pressure $P_T$ as indicated by the filtered motor voltage $V_{MF}$ as it fluctuates within a predefined range, e.g., between about 1.5 and 1.75 volts. However, the DC motor 301 may start operating at high speeds to overcome the loss of supply pressure $P_S$ resulting from a significant leak as would be indicated by the filtered motor voltage $V_{MF}$ when it spikes above the leak voltage $V_L$ and triggers a leak timer 334 to provide a power boost to the DC motor 301. On the other end of the spectrum, the DC motor 301 may slow down to a very slow speed because the system has so little leakage that only a small supply pressure $P_S$ is required to maintain the target pressure $P_T$. This condition is detected when the filtered motor voltage $V_{MF}$ drops below the preset stop voltage $V_S$ and triggers the stop motor timer 318 to simply stop the DC motor 301 to save power when the target pressure $P_T$ is being held at a consistent value. The kick-start timer 324 would then make sure that the DC motor 301 continues running after expiration of the shutdown period $T_{SD}$ and in the absence of a pressure leak signal 320.

In one embodiment, the motor-drive system 300 may be implemented entirely in hardware to avoid additional complexity and regulatory delays associated with implementing the motor-drive system 300 in a software embodiment. The elements of the motor-drive system 300 may be part of a circuit board, integrated circuit, or discretely connected elements. For example, traces, wires, or other conductive mediums may electrically connect the modules of the motor-drive system 300 as described in the block diagram shown in FIG. 3.

Referring now to FIG. 4, a flowchart 400 illustrating a process for controlling a motor that drives a pump for generating a reduced pressure in accordance with an illustrative embodiment of the invention is shown. The process may be implemented by a motor-drive system, such as the motor-drive system 300 described above, or other components of the reduced pressure treatment system 100 such as, for example, the controller 170. The process starts (step 401) by selecting a target pressure $P_T$ to achieve the desired pressure therapy. The process then commences a power-on procedure (step 405) by providing a constant current to the motor and measuring the motor voltage which immediately increases in portion to the speed of the motor and then drops as the motor slows in response to an increasing supply pressure $P_S$. The process may also include a power-on boost procedure (step 410) wherein more power is applied to the motor for a power boost time period ($T_{PB}$) to achieve a more rapid pull-down of the supply pressure $P_S$ For example, the power may be increased by increasing the motor voltage which causes the speed of the motor to increase more rapidly than it would in a normal constant-current condition as described above. This effectively takes the process out of a constant-current condition for the short period of power-on time as the motor will be drawing more current as a result.

When the supply pressure $P_S$ reaches the target pressure $P_T$, the motor slows down with the motor voltage dropping proportionally to a normal operating level in the constant-current mode (step 420). The process then checks to determine whether the speed of the motor as reflected by the motor voltage stays at a normal level or is running too fast or too slow (step 430). If the motor is still running at a normal speed, it continues to do so drawing the constant current in the constant-current mode (step 420). However, when the motor slows down to the point of stalling with the motor voltage dropping proportionally to a low preselected value, i.e., a stall voltage, the process provides a stop motor signal to disconnect the motor from the constant current for a shut-down time period ($T_{SD}$) so that the motor is stopped before it stalls (step 435). The current source is disconnected via a surge-start boost process (440) that restarts the motor after the expiration of the shut-down time period ($T_{SD}$). Essentially, the stall voltage is an indirect indication that the supply pressure $P_S$ has reached the target pressure $P_T$.

After the process provides the stop motor signal, the process returns to the constant-current mode (step 420) after checking whether a user or another control signal turns off the power (step 445) to terminate the process (step 450) and end the treatment. The control signal may be triggered as the result of an event recognized or sensed by a reduced pressure management system such as the ones described above. Referring back to step 430, if the motor is running too fast as may result from a significant leak in the reduced pressure system, the motor voltage will also increase proportionally to a high preselected value, i.e., a leak voltage. If the motor voltage exceeds the leak voltage, the process provides a pressure-leak power boost (step 460) to the motor for a leak-boost time period $T_{(LB)}$ to generate additional supply pressure $P_S$ to compensate for the pressure leak in the system. After the process provides the pressure-leak power boost, the process returns to the constant-current mode (step 420).

The process monitors all of the steps involving timing, i.e., timing steps 410, 435, and 460 (step 465), to determine whether any one of them is active (step 470), i.e., the timer analysis step 470. The timing steps 410, 435, and 460 are considered to be active during the corresponding operational time periods, i.e., the power boost time period ($T_{PB}$), the shut-down time period ($T_{SD}$), and the leak-boost time period ($T_{LB}$). The process provides the output of the timer analysis step 470 to a kick-start timer process (step 480) that provides a kick-start signal 485 to the surge-start boost process 440 under certain conditions. For example, if none of the timing steps are active, the process enables the kick-start signal 485 to the surge-start boost process 440 that briefly stops and restarts the motor to ensure that the motor is running. The time analysis step 470 continues checking whether any of the timing steps become active. If any one of the timing steps become active, the timer analysis step 470 inhibits the kick-start timer process 480 to prevent the kick-start signal 485 from being applied to the surge-start boost process 440 and continues checking whether any of the timing steps are still active. The kick-start signal 485 is asynchronous in that the process continues to enable the signal without regard to the normal operation of the process except when being inhibited as just described.

Figure 6:
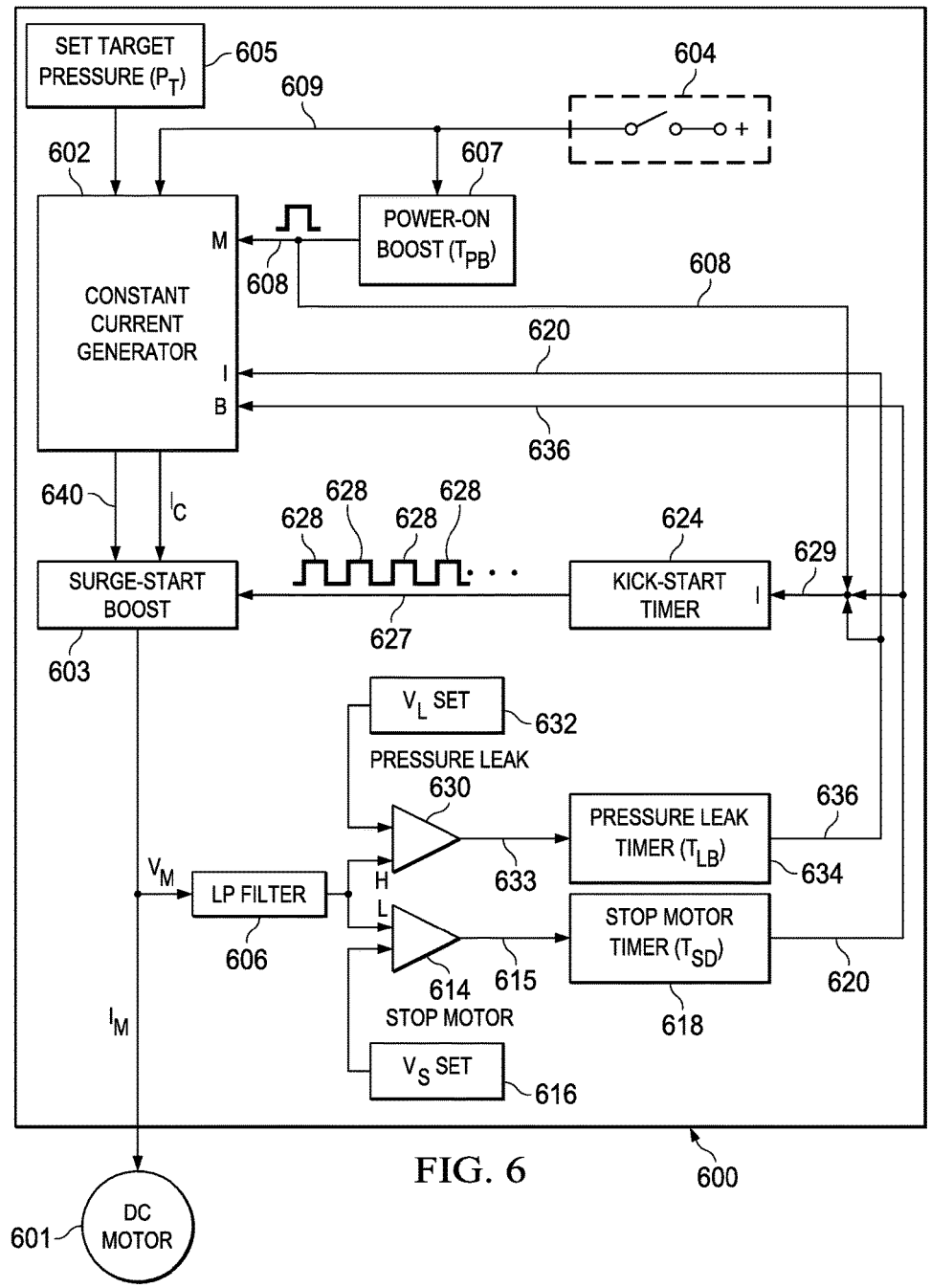
FIG. 6 is a detailed block diagram of a second motor-drive system for providing a constant current to a DC motor that drives a pump in accordance with an illustrative embodiment of the present invention.

Referring now to FIG. 6, another embodiment of a motor-drive system 600 is shown as an illustrative embodiment of the present invention. The motor-drive system 600 may be included as a component of the controller 170 as shown in FIG. 1 or may be structured as a discrete component of the reduced pressure treatment system 100. The motor-drive system 600 may operate in conjunction with or in lieu of the pressure sensor 155. Like the motor-drive system 300 of FIG. 3, the motor-drive system 600 provides a constant current $I_C$ to a motor 601 substantially similar to the DC motor 301 described above that drives a diaphragm pump (not shown). The motor-drive system 600 operates in a substantially similar fashion to the motor-drive system 300 so that the same terminology will be utilized to explain the electrical schematics shown in FIG. 6.

The motor-drive system 600 includes a constant current drive module 602 for providing the constant current $I_C$ to a surge-start boost module 603 and then to the motor 601 as the motor current $I_M$. The target pressure $P_T$ is set by set target pressure module 605 that provides a signal to the constant current drive module 602 for setting a constant current $I_C$ that achieves the desired target pressure $P_T$. The target pressure module 605 includes an input device that can be adjusted by the manufacturer or in some cases a user of a reduced pressure treatment system 100 to vary the constant current $I_C$ for adjusting the target pressure $P_T$ within a range for the pressure therapy that is desired, e.g., 140-150 mmHg. The motor voltage across the motor 601, i.e., the raw motor voltage, $V_M$ (raw), is filtered by a low-pass filter 606 to smooth out any fluctuations and provide a filtered motor voltage, $V_{MF}$. Electrical power is provided to the constant current drive module 602 by a power module 604 that also provides power to a power-on boost module 607.

The motor-drive system 600 may also include several modes of operation such as, for example, a "power-on boost" mode. In this start-up mode, more power is applied to the motor 601 for a set period of time, i.e., the power-on boost period ($T_{PB}$), after starting the motor 601 to achieve a more rapid pull-down of the supply pressure $P_S$, i.e., a higher negative pressure. Fundamentally, the full-rated voltage may be applied to the motor 601 as described above or the motor current may be increased above the constant current $I_C$ to more rapidly increase the speed of the motor 601 so that the desired supply pressure $P_S$ is more quickly achieved. For example, the motor current $I_M$ may be increased by the power-on boost module 607 providing a power-on boost signal 608 to an input terminal (M) of the constant current drive module 602 to increase the motor current $I_M$ to a preset maximum value for a power-on boost period $T_{PB}$. Under a normal constant-current condition, the supply pressure $P_S$ increases to a target pressure $P_T$, e.g., 145 mmHg, in due course; increasing the motor current $T_M$ simply draws down the supply pressure $P_S$ faster. The power-on boost mode increases the motor current $I_M$ applied to the motor 601 in response to a power-on boost signal 608, thereby increasing the rotational speed of the motor 601 so that the supply pressure $P_S$ reaches the target pressure $P_T$ more quickly. The power-on timer module 607 may also provide the power-on boost signal 608 to the inhibit input (I) of the kick-start timer module 624 that will be explained in more detail below.

Referring more specifically to FIG. 5B which is an illustration of the motor current $I_C$, the raw motor voltage $V_M$ (raw), and the filtered motor voltage $V_{MF}$ associated with the supply pressure $P_S$ over the short period of time ($T_X$) shown in FIG. 5A. After the power-on boost period ($T_{PB}$) on start-up times out, the motor-drive system 600 returns to the constant-current condition where the motor current $I_M$ is about equal to the constant current $I_C$ setting as shown in FIG. 5B. The motor-drive system 300 remains in the constant current condition for a variable period of time ($T_{ON}$) depending on how long it takes the supply pressure $P_S$ to reach the target pressure $P_T$. As the dressing 115 develops more leaks over time, for example, the motor-drive system 600 works harder to combat the leaks so that the time-on periods $T_{ON}$ last longer as illustrated by the time-periods T1, T2, T3, and T4 where the time-on period T4 is longer than the time-on period T1.

When the supply pressure $P_S$ reaches the target pressure $P_T$, the motor-drive system 600 is further configured to operate in a mode of operation wherein the motor 601 is stopped if the rotational speed is too slow, i.e., the "stop-motor-if-slow" mode. Essentially, the motor-drive system 600 includes circuitry that shuts down the pump 601 for a set period of time. After the shut-down period ($T_{SD}$), the filtered motor voltage $V_{MF}$ drops below the stall voltage $V_S$ at turn-off time $t_1$ as described above and shown in FIG. 5B. The low-pass filter 606 provides the filtered motor voltage $V_{MF}$ to the low-voltage reference input (L) of a stop-motor or stall comparator 614 that compares the filtered motor voltage $V_{MF}$ to the stall voltage $V_S$. The manufacturer or user sets the stall voltage $V_S$ utilizing set point module 616 that provides the desired stall voltage $V_S$ to the stall comparator 614.

The stall comparator 614 provides a stall condition signal 615 to a stop-motor or stall timer module 618 when the motor voltage $V_M$ drops below the stall voltage $V_S$ that triggers the stall timer module 618 to run for a fixed period of time, i.e., the shut-down period ($T_{SD}$). During the shut-down period $T_{SD}$, the stall timer module 618 provides a stop signal 620 to the inhibit input (I) of the constant current drive module 602 to reduce the motor current ($I_M$) to zero as indicated, for example, by the off-times ($t_{off}$) at $t_1$, $t_3$, $t_5$, and $t_7$ marking the end of the respective time-on periods (T1-T4). After the shut-down period ($T_{SD}$) expires, the stop signal 620 is removed so that the constant current generator 602 triggers the surge-start boost 603 to reconnect the motor 601 to the current source at on-times ($t_{on}$) $t_2$, $t_4$, $t_6$, and $t_8$ causing a spike in the motor current $I_M$ and the raw motor voltage $V_M$ (raw), but not in the filtered motor voltage $V_{MF}$ as described above.

For example, the stall voltage $V_S$ may be set at a value of about 1.25 volts so that the stall comparator 614 provides a stall condition signal to the stall timer module 618 when the filtered motor voltage $V_{MF}$ drops below the stall voltage $V_S$ at off-times ($t_{off}$) $t_1$, $t_3$, $t_5$, and $t_7$ as shown in FIG. 5B. The stall timer module 618 provides a stop signal 620 each time, and each time shuts down the motor 601 such that the motor voltage $V_M$ drops to zero for the shut-down period $T_{SD}$ in the stop-motor-if-slow mode. After the shut-down time period ($T_{SD}$) expires, the motor 601 restarts at a lower power level and the filtered motor voltage $V_{MF}$ ramps up at on-times $t_2$, $t_4$, $t_6$, and $t_8$ to an operational voltage greater than the stall voltage $V_S$ which may be a value of about 1.5 volts, as indicated by $V_M(1)$, $V_M(2)$, $V_M(3)$, and $V_M(4)$. Thus, a complete operational cycle for the motor 601 includes the variable time-on periods $T_{ON}$ (T1, T2, T3, and T4) during the constant-current modes and the constant shut-down time periods $T_{SD}$ as shown in FIG. 5B. The stop signal 620 is also provided to the inhibit input (I) the kick-start timer module 624.

The motor-drive system 600 also includes a kick-start mode of operation to ensure that the pump 601 does not stop for too long at any time during the operational cycle of the motor 601 as long as the motor-drive system 600 is not in the power-on boost mode or the stop-motor-if-slow mode. Both the power-on boost signal 608 and the stop signal 620 may also be applied to the inhibit input (I) of the kick-start timer module 624 as described above. The kick-start timer 624 provides a kick-start timing signal 627 to the surge-start boost module 603 causing it to operate as described above. The kick-start timing signal 627 is an asynchronous signal that provides successive pulses 628 to the surge-boost module 603 when not inhibited by any of the other operational modes at fixed frequency or time period ($T_{KS}$). Each pulse 628 triggers the surge-start boost module 603 to briefly stop and restart the motor 601 ensuring that the motor 601 does not stop for an indefinite period of time. The kick-start timer module 624 continues providing the kick-start timing signal 627 in the absence of a power-on boost signal 608 or a stop signal 620. However, the presence of either signal provides an inhibit signal 629 that inhibits the kick-start timer module 624.

The inhibit condition occurs because the kick-start timer 624 is not needed when the motor 601 is running fast in the power-on boost mode or stopped. Consequently, the power-on boost signal 608 and the stop signal 620 inhibit the kick-start timer 624 to disable the surge-start boost module 603 for their respective time periods. The power-on boost module 607 may be structured to time out on start-up before the kick-start timing signal commences, so that the power-on boost signal 608 need not be applied to inhibit the kick-start timer module 624. After the shut-down period $T_{SD}$ and the power-on boost period $T_{PB}$ expire, the stop signal 620 and the power-on boost signal 608 no longer inhibit the kick-start timing signal 627 so that the surge-start boost module 603 is triggered by the pulses 628 of the kick-start timing signal 627 as illustrated by the small negative spikes 505 that occur in the filtered motor voltage $V_M$ (filter) during the constant current mode of operation to ensure that the surge-start boost module 603 is providing power to the motor 601. Several negative spikes 505 may occur during time-on period $T_{ON}$ of a constant current mode such as during the time-on period T5. The kick-start timer 624 and the surge-start boost module 603 function as a watchdog timer to ensure that the motor 601 continues running in the constant-current mode and, as such, they function as a safety feature that is not necessary for the operation of the motor-drive system 600.

Referring again to FIG. 5B for an example, the stop signal 620 occurs at the off-times ($t_{off}$) at $t_1$, $t_3$, $t_5$, and $t_7$ which inhibits the kick-start timing signal 627 so that the surge-start boost module 603 does not energize the motor 601. When the shut-down time period $T_{SD}$ expires at the on-times ($t_{on}$) $t_2$, $t_4$, $t_6$, and $t_8$, the kick-start timing signal 627 is no longer inhibited so that it continues to trigger the surge-start boost module 603 to ensure that the motor 601 restarts to maintain the supply pressure $P_S$ in the proximity of the target pressure $P_T$. After the motor 601 restarts, the filtered motor voltage $V_{MF}$ rises back to an operational speed equivalent to a motor voltage of about 1.5 volts. The stop-motor mode maintains the supply pressure $P_S$ at or near the target pressure $P_T$ in the absence of significant leakage to compensate for the normal level of operational leakage from the reduced pressure treatment system 100. The kick-start mode ensures that the motor 601 continues running when operating at a low power, i.e., fixed current and low voltage, as should occur at the target pressure $P_T$.

As indicated above, the stop-motor mode maintains the supply pressure $P_S$ in the proximity of the target pressure $P_T$ in the absence of significant leakage. When the leakage is significant and causes a rapid decrease in the applied pressure at the tissue site 105, the speed of the motor increases in response to the reduced load on the pump as indicated by the filtered motor voltage $V_{MF}$ that rises at the same time as indicated by the motor voltage $V_M$(5). In one embodiment of the motor-drive system 600, the manufacturer or user of the system selects a ceiling for the motor voltage $V_M$ at a specific value, i.e., a leak voltage ($V_L$). When the filtered motor voltage $V_{MF}$ exceeds the leak voltage ($V_L$) by any significant design margin, a significant leak condition is present in the system.

Thus, the motor-drive system 600 also includes a "power-boost-if-fast" mode of operation which includes modules for providing an indication of significant leaks in the system. The low-pass filter 606 also provides the filtered motor voltage $V_{MF}$ to the high-reference voltage input (H) of a pressure leak comparator 630. The manufacturer or user sets the leak voltage $V_L$ at an input device 632 that provides a leak signal reflective of the leak voltage $V_L$ to the leak comparator 630. When the motor voltage $V_M$ is equal to or greater than the leak voltage $V_L$, the leak comparator 630 provides a leak indicator signal 633 to a leak timer module 634 which provides a power boost signal 636 to the boost input (B) of the constant current drive module 602 and the inhibit input (I) of the kick-start timer 624 to disable the kick-start timer module 624 when present as described above. The constant current drive module 602 provides a power boost signal 640 to the surge-start boost module 603 which drives the motor 601 at an increased power level, i.e., the boost leak power.

The boost leak power may be generated by either increasing the motor current $I_M$ beyond the preset constant current $I_C$ or by again increasing the motor voltage $V_M$ applied to the motor 601. The boost leak power generates additional supply pressure $P_S$ to compensate for a significant leak in the reduced pressure treatment system 100. The leak timer module 634 times out after a leak boost time period ($T_{LB}$) during which the boost leak power is applied to the motor 601. After the leak boost time period ($T_{LB}$) expires, the motor 601 should return to its normal speed as indicated by the operational motor voltage $V_M$ associated with that speed if the significant leak is corrected. The pressure leak timer 634 also provides the power boost signal 636 to the kick-start timer 624 to again trigger the inhibit signal 629 to inhibit the kick-start timing signal 627 and disable the surge-start boost module 603 as described above. After the leak boost time period $T_{LB}$ has expired, the kick-start timing signal 627 is no longer inhibited so that it continues to trigger the surge-start boost module 603 in the absence of a stop signal 620 as described above.

Referring again to FIG. 5B for an example of the operation of the power-boost-if-fast mode, the manufacturer or a user may set the leak voltage $V_L$ at a value of 2.0 volts. If a significant leak occurs at time $t_9$, the supply pressure $P_S$ will drop below the target pressure $P_T$ to value such as, for example, $P_S$(2), also shown in the compressed timeline of FIG. 5A at about 100 mmHg of reduced pressure. Consequently, the motor 601 runs faster to compensate for the lost pressure which causes the filtered motor voltage $V_{MF}$ to increase and eventually exceed the leak voltage $V_L$ at 507. When the filtered motor voltage $V_{MF}$ exceeds the leak voltage $V_L$, the leak comparator 630 triggers the leak timer 634 which applies the boost leak power to the constant current generator 602 by increasing, for example, the motor current $I_M$ above the constant current $I_C$ to a value $I_{PB}$ for the leak boost time period ($T_{LB}$). The boost leak power causes the motor 601 to run even faster to overcome the loss of supply pressure $P_S$ resulting from the leak and increase the supply pressure $P_S$ back up to, and perhaps overshooting, the target pressure $P_T$ as indicated by supply pressure $P_S$(3). If the supply pressure $P_S$ remains in the proximity of the target pressure $P_T$, the filtered motor voltage $V_{MF}$ provides an indication that the leak has been overcome because the filtered motor voltage $V_{MF}$ drops below the leak voltage $V_L$ back down below the stall voltage $V_S$ after the leak-boost time period ($T_{LB}$) expires as indicated by motor voltage V(6).

Nevertheless, the power-boosted motor 601 may not be able to overcome a significant leak that persists and the corresponding loss of supply pressure $P_S$ after the expiration of the leak boost time period ($T_{LB}$). This situation would be indicated if the pressure leak indicator 630 again provides a leak-condition signal 633 because the motor voltage $V_M$ at time $t_{10}$ is still greater than the leak voltage $V_L$ as indicated by motor voltage $V_M$(7). This inferentially indicates that the supply pressure $P_S$ has not yet reached the target pressure $P_C$, or reached the target pressure $P_T$ and fallen below the target pressure $P_T$ again, as indicated by supply pressure $P_S$(4). Consequently, the power-on boost signal 636 retriggers the constant current generator 602 to provide the boost leak power to the motor 601. The leak comparator 630 stops triggering the leak timer 634 only when the filtered motor voltage $V_{MF}$ drops below the leak voltage $V_L$. In some cases, the leak may be bad enough so that the supply pressure $P_S$ cannot compensate for the lost pressure and never reaches the target pressure $P_T$ as indicated by a filtered motor voltage $V_{MF}$ that never drops below the leak voltage $V_L$. In such cases, the pressure sensor 155 may be used to confirm that a significant leak is still present as indicated by the indicator 172. Although the pressure sensor 155 is not necessary for the operation of the invention, it can provide some backup to ensure the system is properly operating.

Thus, the motor 601 normally operates at a speed sufficient to maintain the target pressure $P_T$ as indicated by the filtered motor voltage $V_{MF}$ as it fluctuates within a predefined range, e.g., between about 1.5 and 1.75 volts. However, the motor 601 may start operating at high speeds to overcome the loss of supply pressure $P_S$ resulting from a significant leak as would be indicated by the filtered motor voltage $V_{MF}$ when it spikes above the leak voltage $V_L$ and triggers a leak timer 634 to provide a power boost to the motor 601. On the other end of the spectrum, the motor 601 may slow down to a very slow speed because the system has so little leakage that only a small supply pressure $P_S$ is required to maintain the target pressure $P_T$. This condition is detected when the filtered motor voltage $V_{MF}$ drops below the preset stop voltage Vs and triggers the stop motor timer 618 to simply stop the motor 601 to save power when the target pressure $P_T$ is being held at a consistent value. The kick-start timer 624 would then make sure that the motor 601 continues running after expiration of the shutdown period $T_{SD}$ and in the absence of a pressure leak signal 620.

In one embodiment, the motor-drive system 600 may be implemented entirely in hardware to avoid additional complexity and regulatory delays associated with implementing the motor-drive system 600 in a software embodiment. The elements of the motor-drive system 600 may be part of a circuit board, integrated circuit, or discretely connected elements. For example, traces, wires, or other conductive mediums may electrically connect the modules of the motor-drive system 600 as described in the block diagram shown in FIG. 6.

Figure 7A:
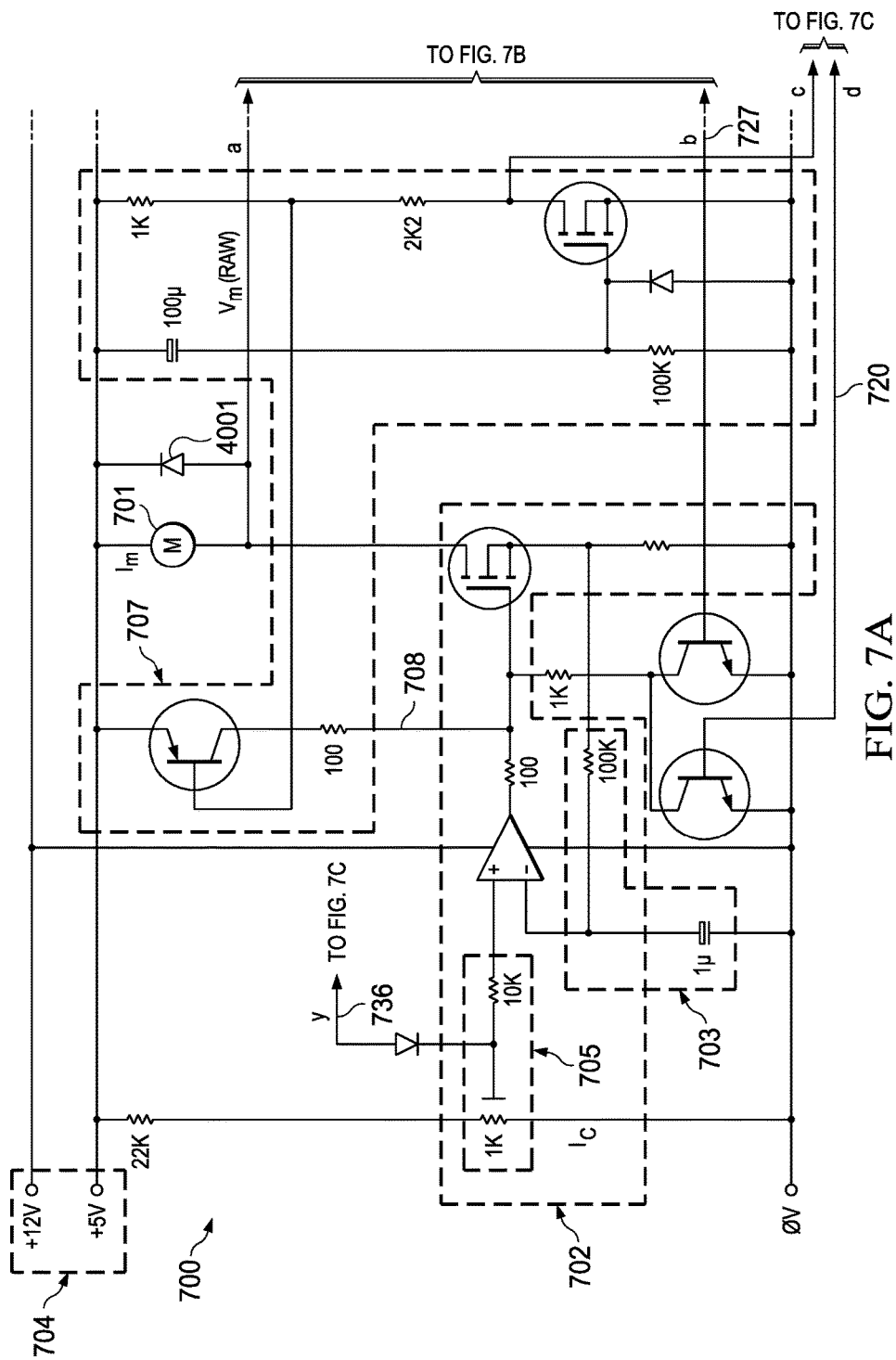
FIGS. 7A-7C is a detailed circuit schematic of a third motor-drive system for providing a constant current to a DC motor that drives a pump in accordance with an illustrative embodiment of the present invention with some portions similar to the motor-drive system of FIG. 6 in accordance with an illustrative embodiment of the present invention.
Figure 7B:
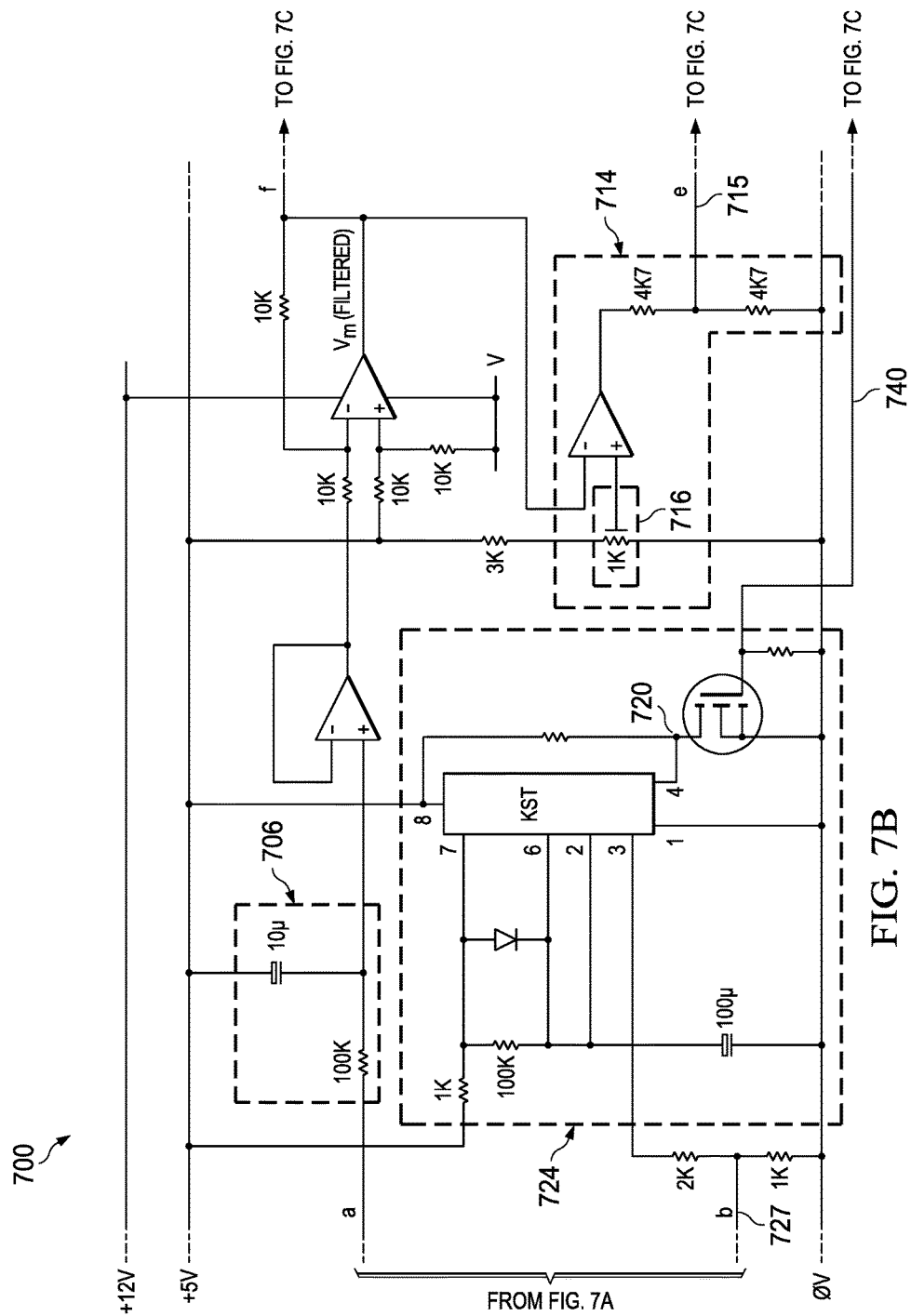
Figure 7C:
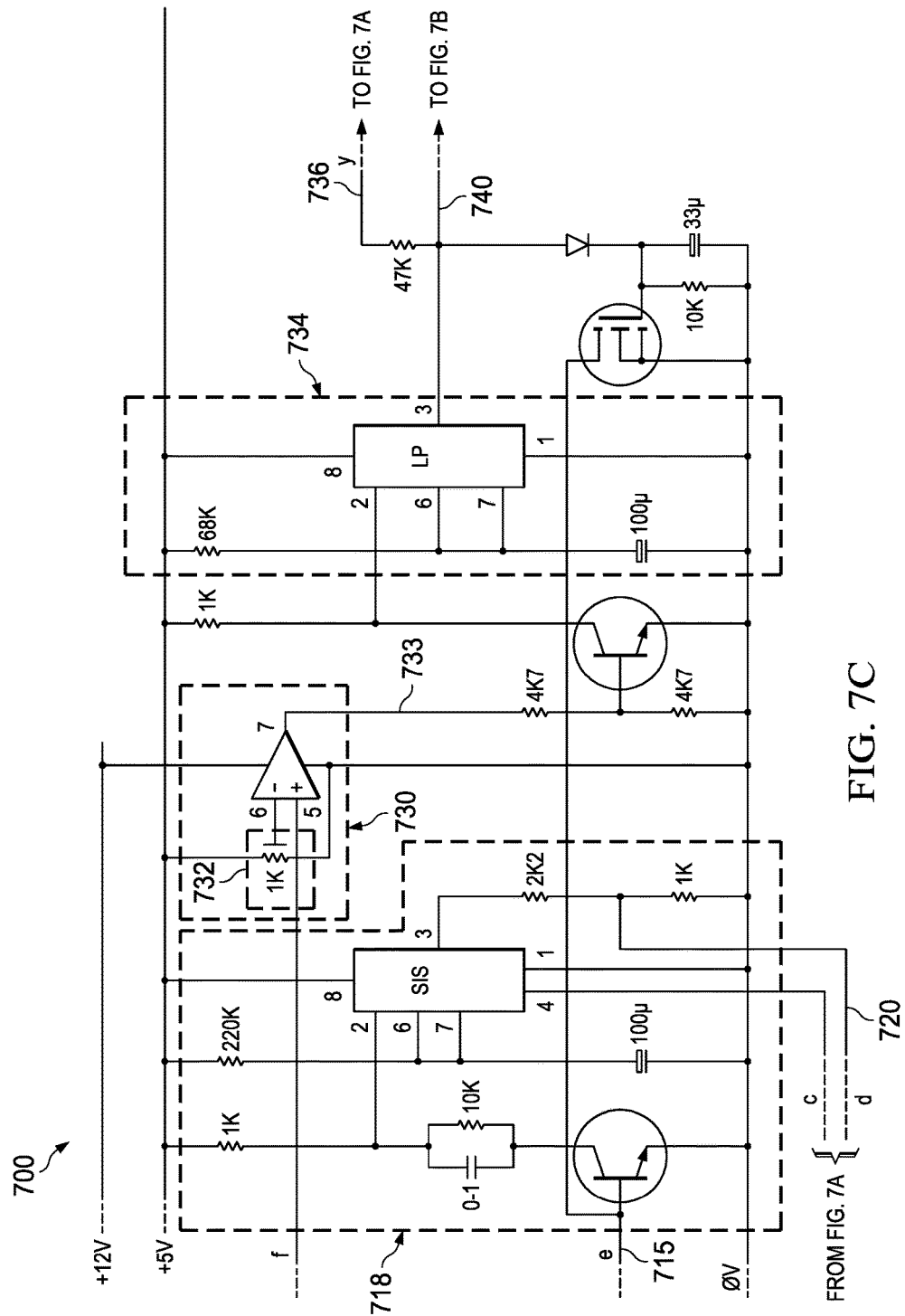

Referring now to FIGS. 7A-C, another embodiment of a motor-drive system 700 is shown as an illustrative embodiment of the present invention. The motor-drive system 700 may be included as a component of the controller 170 as shown in FIG. 1 or may be structured as a discrete component of the reduced pressure treatment system 100. The motor-drive system 700 may operate in conjunction with or in lieu of the pressure sensor 155. Like the motor-drive system 600 of FIG. 6, the motor-drive system 700 provides a constant current $I_C$ to a motor 701 substantially similar to the motor 601 described above that drives a diaphragm pump (not shown). The motor-drive system 700 operates in a substantially similar fashion to the motor-drive system 600 and essentially is a more detailed schematic of the block diagram shown in FIG. 6 so that the same terminology and a similar number scheme will be utilized to explain the electrical schematics shown in FIGS. 7A to 7C. It is to be understood, however, that the symbols and signals shown in FIG. 6 may not correspond exactly to the components and circuitry shown in FIGS. 7A to 7C. For example, inhibit signals may be implicit within a specific component of the circuitry.

Regarding the numbering scheme, for example, the last two digits of the reference number will be the same so that a power-on timer module 707 to be described in FIG. 7A is generally associated with the power-on timer module 607 referred to in FIG. 6 as a component of that module. The symbols used in these schematics are known to those skilled in the art, many of which show specific values that are exemplary and can be adjusted as needed to achieve the desired target pressure and to maintain the supply pressure $P_S$ in the desired range. The diodes may all be a 4148 type diode such as the ones supplied by Fairchild except where indicated otherwise. The transistors may all be either a 547 or 557 type transistor such as the ones supplied by Fairchild except where indicated otherwise. The field effect transistors may all be a 170 type transistor such as the ones supplied by Fairchild except where indicated otherwise. The operational amplifiers may all be a type 660 operational amplifier such as the ones supplied by National Semiconductor except where indicated otherwise. The timers may all be 555 timers such as the ones supplied by National Semiconductor except where indicated otherwise. It should be apparent to one skilled in the art that other components may be used to achieve similar results contemplated by the invention including variations of the circuit's architecture. Hence, the invention is not limited by the specific structure and components associated with the motor-drive system 700 as shown in FIGS. 7A to 7C as one skilled in the art would understand.

The motor-drive system 700 includes a constant current drive module 702 for providing the constant current $I_C$ to a surge-start boost module 703 and then to the motor 701 as the motor current $I_M$. The target pressure $P_T$ is set by set target pressure module 705 that provides a signal to the constant current drive module 702 for setting a constant current $I_C$ that achieves the desired target pressure $P_T$. The target pressure module 705 includes an input device that can be adjusted by the manufacturer or in some cases a user of a reduced pressure treatment system 100 to vary the constant current $I_C$ for adjusting the target pressure $P_T$ within a range for the pressure therapy that is desired, e.g., 140-150 mmHg. The motor voltage across the motor 701, i.e., the raw motor voltage, $V_M$ (raw), is filtered by a low-pass filter 706 to smooth out any fluctuations in the raw motor voltage $V_M$ (raw) and provide a filtered motor voltage, $V_{MF}$.

The constant current drive module 702 supplies power to the motor 701 and includes an operational amplifier and transistor circuit as shown that maintains the voltage on the series-pass resistor equal to that on the variable resistor of the target pressure module 705 by adjusting the current through the motor 701. The surge-start boost module 703 includes an RC circuit that provides a brief pulse of high energy to overcome the friction of the motor 701 whenever power is reapplied to the motor 701. The power module 704 provides DC power to the entire motor-drive system 700 including the constant current drive module 702. The target pressure module 705 includes a variable resistor for setting the constant current ($I_C$) provided by the constant current generator 702.

The motor-drive system 700 may also include several modes of operation such as, for example, a "power-on boost" mode. In this start-up mode, more power is applied to the motor 701 for a set period of time, i.e., the power-on boost period ($T_{PB}$), after starting the motor 701 to achieve a more rapid pull-down of the supply pressure $P_S$, i.e., a higher negative pressure. Fundamentally, the full-rated voltage may be applied to the motor 701 as described above or the motor current $I_M$ may be increased above the constant current $I_C$ to more rapidly increase the speed of the motor 701 so that the desired supply pressure $P_S$ is more quickly achieved. Therefore, the motor-drive system 700 also includes a power-on boost module 707 comprising an RC network and associated transistors which apply full power to the motor 701 when switched on during the power-on boost period ($T_{PB}$).

For example, the motor current $I_M$ may be increased by the power-on boost module 707 providing a power-on boost signal 708 to an input terminal (M) of the constant current drive module 702 to increase the motor current $I_M$ to a preset maximum value for a power-on boost period $T_{PB}$. Under a normal constant-current condition, the supply pressure $P_S$ increases to a target pressure $P_T$, e.g., 145 mmHg, in due course; increasing the motor current $I_M$ simply draws down the supply pressure $P_S$ faster. The power-on boost mode increases the motor current $I_M$ applied to the motor 701 in response to a power-on boost signal 708, thereby increasing the rotational speed of the motor 701 so that the supply pressure $P_S$ reaches the target pressure $P_T$ more quickly. The power-on boost module 707 may also provide the power-on boost signal 708 to the inhibit input (I) of the kick-start timer module 724 that will be explained in more detail below.

Referring more specifically to FIG. 5B which is an illustration of the motor current $I_C$, the raw motor voltage $V_M$ (raw), and the filtered motor voltage $V_{MF}$ associated with the supply pressure $P_S$ over the short period of time ($T_X$) shown in FIG. 5A. After the power-on boost period ($T_{PB}$) on start-up times out, the motor-drive system 700 returns to the constant-current condition where the motor current $T_M$ is about equal to the constant current condition for a variable period of time ($T_{ON}$) depending on how long it takes the supply pressure $P_S$ to reach the target pressure $P_T$. As the dressing 115 develops more leaks over time, for example, the motor-drive system 700 works harder to combat the leaks so that the time-on periods $T_{ON}$ last longer as illustrated by the time-periods T1, T2, T3, and 14 where the time-on period T4 is longer than the time-on period T1.

When the supply pressure $P_S$ reaches the target pressure $P_T$, the motor-drive system 700 is further configured to operate in a mode of operation wherein the motor 701 is stopped if the rotational speed is too slow, i.e., the "stop-motor-if-slow" mode. Essentially, the motor-drive system 700 includes circuitry that shuts down the pump 701 for a set period of time. After the shut-down period ($T_{SD}$), the filtered motor voltage $V_{MF}$ drops below the stall voltage $V_S$ at turn-off time $t_1$ as described above and shown in FIG. 53. The low-pass filter 706 provides the filtered motor voltage $V_{MF}$ to the low-voltage reference input (L) of a stop-motor or stall comparator 714 that compares the filtered motor voltage $V_{MF}$ to the stall voltage $V_S$. The manufacturer or user sets the stall voltage $V_S$ utilizing set point module 716 that provides the desired stall voltage $V_S$ to the stall comparator 714.

The stall comparator 714 provides a stall condition signal 715 to a stop-motor or stall timer module 718 when the motor voltage $V_M$ drops below the stall voltage $V_S$ that triggers the stall timer module 718 to run for a fixed period of time, i.e., the shut-down period ($T_{SD}$). When the stall timer module 718 times out after the shut-down period $T_{SD}$, it provides a stop signal 720 to the inhibit input (I) of the constant current drive module 702 to reduce the motor current ($I_M$) to zero as indicated, for example, by the off-times ($t_{off}$) at $t_1$, $t_3$, $t_5$, and $t_7$ marking the end of the respective time-on periods (T1-T4). After the shut-down period ($T_{SD}$) expires, the stop signal 720 is removed so that the constant current generator 702 triggers the surge-start boost 703 to reconnect the motor 701 to the current source at on-times ($t_{on}$) $t_2$, $t_4$, $t_6$, and $T_8$ causing a spike in the motor current $I_M$ and the raw motor voltage $V_M$ (raw), but not in the filtered motor voltage $V_{MF}$ as described above.

For example, the stall voltage $V_S$ may be set at a value of about 125 volts so that the stall comparator 714 provides a stall condition signal 715 to the stall timer module 718 when the filtered motor voltage $V_{MF}$ drops below the stall voltage $V_S$ at off-times ($t_{off}$) $t_1$, $t_3$, $t_5$, and $t_7$ as shown in FIG. 5B. The stall timer module 718 provides a stop signal 720 each time, and each time shuts down the motor 701 such that the motor voltage $V_M$ drops to zero for the shut-down period $T_{SD}$ in the stop-motor-if-slow mode. After the shut-down time period ($T_{SD}$) expires, the motor 701 restarts at a lower power level and the filtered motor voltage $V_{MF}$ ramps up at on-times $t_2$, $t_4$, $t_6$, and $t_8$ to an operational voltage greater than the stall voltage $V_S$ which may be a value of about 15 volts, as indicated by $V_M(1)$, $V_M(2)$, $V_M(3)$, and $V_M(4)$. Thus, a complete operational cycle for the motor 701 includes the variable time-on periods $T_{ON}$ (T1, T2, T3, and T4) during the constant-current modes and constant shut-down time period $T_{SD}$ as shown in FIG. 5B. The stop signal 720 is also provided to the inhibit input (I) to kick-start timer module 724.

The motor-drive system 700 also includes a kick-start mode of operation to ensure that the pump 701 does not stop for too long at any time during the operational cycle of the motor 701 as long as the motor-drive system 700 is not in the power-on boost mode or the stop-motor-if-slow mode. Both the power-on boost signal 708 and the stop signal 720 may also be applied to the inhibit input (I) of the kick-start timer module 724 as described above. The kick-start timer 724 provides a kick-start timing signal 727 to the surge-start boost module 703 causing it to operate as described above. The kick-start timing signal 727 is an asynchronous signal that provides successive pulses 728 to the surge-boost module 703 when not inhibited by any other operational modes at a fixed frequency or time period ($T_{KS}$). Each pulse 728 triggers the surge-start boost module 703 to briefly stop and start the motor 701 ensuring that the motor 701 does not stop for an indefinite period of time. The kick-start timer module 724 continues providing the kick-start timing signal 727 in the absence of a power-on boost signal 708 or a stop signal 720. However, the presence of either signal provides and the inhibit signal 729 that inhibits the kick-start timer module 724.

The inhibit condition occurs because the kick-start timer 724 is not needed when the motor 701 is running fast in the power-on boost mode or stopped. Consequently, the power-on boost signal 708 and the stop signal 720 inhibit the kick-start timer 724 to disable the surge-start boost module 703 for their respective time periods. The power-on boost module 707 may be structured to time out on start-up before the kick-start timing signal commences, so that the power-on boost signal 708 need not be applied to inhibit the kick-start timer module 724. After the shut-down period $T_{SD}$ and the power-on boost period $T_{PB}$ expire, the stop signal 720 and the power-on boost signal 708 no longer inhibit the kick-start timing signal 727 so that the surge-start boost module 703 is triggered by the pulses 728 of the kick-start timing signal 727 as illustrated by the small negative spikes 505 that occur in the filtered motor voltage $V_{MF}$ during the constant current mode of operation to ensure that the surge-start boost module 703 is providing power to the motor 701. Several negative spikes 505 may occur during time-on period $T_{ON}$ of a constant current mode such as during the time-on period T5. The kick-start timer 724 and the surge-start boost module 703 function as a watchdog timer to ensure that the motor 701 continues running in the constant-current mode and, as such, they function as a safety feature that is not necessary for the operation of the motor-drive system 700.

Referring again to FIG. 5B for an example, the stop signal 720 occurs at the off-times ($t_{off}$) at $t_1$, $t_3$, $t_5$, and $t_7$ which inhibits the kick-start timing signal 727 so that the surge-start boost module 703 does not energize the motor 701. When the shut-down time period $T_{SD}$ expires at the on-times ($t_{on}$) $t_2$, $t_4$, $t_6$, and $t_8$, the kick-start timing signal 727 is no longer inhibited so that it continues to trigger the surge-start boost module 703 to ensure that the motor 701 restarts to maintain the supply pressure $P_S$ in the proximity of the target pressure $P_T$. After the motor 701 restarts, the filtered motor voltage $V_{MF}$ rises back to an operational speed equivalent to a motor voltage of about 1.5 volts. The stop-motor mode maintains the supply pressure $P_S$ at or near the target pressure $P_T$ in the absence of significant leakage to compensate for the normal level of operational leakage from the reduced pressure treatment system 100. The kick-start mode ensures that the motor 701 continues running when operating at a low power, i.e., fixed current and low voltage, and should occur at the target pressure $P_T$.

As indicated above, the stop-motor mode maintains the supply pressure $P_S$ in the proximity of the target pressure $P_T$ in the absence of significant leakage. When the leakage is significant and causes a rapid decrease in the applied pressure at the tissue site 105, the speed of the motor increases in response to the reduced load on the pump as indicated by the filtered motor voltage $V_{MF}$ that rises at the same time as indicated by the motor voltage $V_M(S)$. In one embodiment of the motor-drive system 700, the manufacturer or user of the system selects a ceiling for the motor voltage $V_M$ at a specific value, i.e., a leak voltage ($V_L$). When the filtered motor voltage $V_{MF}$ exceeds the leak voltage ($V_L$) by any significant design margin, a significant leak condition is present in the system. Thus, the motor-drive system 700 also includes a "power-boost-if-fast" mode of operation which includes modules for providing an indication of significant leaks in the system. The low-pass filter 706 also provides the filtered motor voltage $V_{MF}$ to the high-reference voltage input (H) of a pressure leak comparator 730. The manufacturer or user sets the leak voltage $V_L$ at an input device 732 that provides a leak signal reflective of the leak voltage $V_L$ to the leak comparator 730. When the motor voltage $V_M$ is equal to or greater than the leak voltage $V_L$, the leak comparator 730 provides a leak indicator signal 733 to a leak timer module 734 which provides a power boost signal 736 to the boost input (B) of the constant current drive module 702 and the inhibit input (I) of the kick-start timer 724 to disable the kick-start timer module 724 when present as described above. The constant current drive module 702 provides a power boost signal 740 to the surge-start boost module 703 which drives the motor 701 at an increased power level, i.e., the boost leak power.

The boost leak power may be generated by either increasing the motor current $I_M$ beyond the preset constant current $I_C$ or by again increasing the motor voltage $V_M$ applied to the motor 701. The boost leak power generates additional airflow to compensate for a significant leak in the reduced pressure treatment system 100. The leak timer module 734 times out after a leak boost time period ($T_{LB}$) during which the boost leak power is applied to the motor 701. After the leak boost time period ($T_{LB}$) expires, the motor 701 should return to its normal speed as indicated by the operational motor voltage $V_M$ associated with that speed if the significant leak is corrected. The pressure leak timer 734 also provides the power boost signal 736 to the kick-start timer 724 to again trigger the inhibit signal 629 to inhibit the kick-start timing signal 727 and disable the surge-start boost module 703 as described above when the power boost signal 740 is being applied to the surge-start boost module 703. After the leak boost time period $T_{LB}$ has expired, the kick-start timing signal 727 is no longer inhibited so that it continues to trigger the surge-start boost module 703 in the absence of a stop signal 620 as described above.

Referring again to FIG. 5B for an example of the operation of the power-boost-if-fast mode, the manufacturer or a user may set the leak voltage $V_L$ at a value of 2.0 volts. If a significant leak occurs at time $t_9$, the supply pressure $P_S$ will drop below the target pressure $P_T$ to value such as, for example, $P_S(2)$ which causes the motor 701 to run faster. As a result, the filtered motor voltage $V_{MF}$ will also increase and eventually will exceed the leak voltage $V_L$ at 507 which causes the leak comparator 730 to trigger the leak timer 734. When the leak timer 734 is triggered, the boost leak power is applied to the constant current generator 702 by increasing, for example, the motor current $I_M$ above the constant current $I_C$ to a value $I_{PB}$ for the leak boost time period ($T_{LB}$). The boost leak power causes the motor 701 to run even faster to overcome the loss of supply pressure $P_S$ resulting from the leak and increase the supply pressure $P_S$ back up to the target pressure $P_T$ as indicated by supply pressure $P_S(3)$. If the supply pressure $P_S$ remains in the proximity of the target pressure $P_T$, the filtered motor voltage $V_{MF}$ provides an indication that the leak has been overcome because the filtered motor voltage $V_{MF}$ drops below the leak voltage $V_1$, back down below the stall voltage $V_S$ after the leak-boost time period ($T_{LB}$) expires as indicated by motor voltage V(6).

Nevertheless, the power-boosted motor 701 may not be able to overcome a significant leak that persists and the corresponding loss of supply pressure $P_S$ after the expiration of the leak boost time period ($T_{LB}$). This situation would be indicated if the pressure leak indicator 730 again provides a leak-condition signal 733 because the motor voltage $V_M$ at time $t_{10}$ is still greater than the leak voltage $V_L$ as indicated by the motor voltage $V_M(7)$. This inferentially indicates that the supply pressure $P_S$ has not yet reached the target pressure $P_T$, or reached the target pressure $P_T$ and fallen below the target pressure $P_T$ again, as indicated by supply pressure $P_S(4)$. Consequently, the power-on boost signal 736 retriggers the constant current generator 702 to provide the boost leak power to the motor 701. The leak comparator 730 stops triggering the leak timer 734 only when the filtered motor voltage $V_{MF}$ drops below the leak voltage $V_L$. In some cases, the leak may be bad enough so that the supply pressure $P_S$ cannot compensate for the lost pressure and never reaches the target pressure $P_T$ as indicated by a filtered motor voltage $V_{MF}$ that never drops below the leak voltage $V_L$. In such cases, the pressure sensor 155 may be used to confirm that a significant leak is still present as indicated by the indicator 172. Although the pressure sensor 155 is not necessary for the operation of the invention, it can provide some backup to ensure the system is properly operating.

Thus, the motor 701 normally operates at a speed sufficient to maintain the target pressure $P_T$ as indicated by the filtered motor voltage $V_{MF}$ as it fluctuates within a predefined range, e.g., between about 1.5 and 1.75 volts. However, the motor 701 may start operating at high speeds to overcome the loss of supply pressure $P_S$ resulting from a significant leak as would be indicated by the filtered motor voltage $V_{MF}$ when it spikes above the leak voltage $V_L$ and triggers a leak timer 734 to provide a power boost to the motor 701. On the other end of the spectrum, the motor 701 may slow down to a very slow speed because the system has so little leakage that only a small supply pressure $P_S$ is required to maintain the target pressure $P_T$. This condition is detected when the filtered motor voltage $V_{MF}$ drops below the preset stop voltage $V_S$ and triggers the stop motor timer 718 to simply stop the motor 701 to save power when the target pressure $P_T$ is being held at a consistent value. The kick-start timer 724 would then make sure that the motor 701 continues running after expiration of the shutdown period $T_{SD}$ and in the absence of a pressure leak signal 720.

The flowcharts and block diagrams in the different depicted embodiments illustrate the architecture, functionality, and operation of some possible implementations of the apparatus and methods. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The illustrative embodiments may be configured to be a light weight and low cost system that consumes less power than currently used reduced pressure treatment systems. The reductions in size and weight are particularly important when the system is to be used to treat low-severity wounds and wounds on ambulatory patients. These wounds and patients require a system that is unobtrusive and lightweight so that discomfort to the patient and hindrance of movement are minimized.

One way in which cost, weight, and power consumption are minimized is through the use of only one sensor to measure pressure. As previously mentioned, traditional systems typically use two pressure sensors, one to measure pressure at the tissue site and one to measure pressure at the reduced pressure source. However, the elimination of the pressure sensor measuring pressure at the reduced pressure source allows significant reductions in the amount of electronic circuitry required and also the amount of power consumed by the system. Additionally, any circuitry and software used to compare the two sensor readings is eliminated. In addition, the illustrative embodiments enable the application of a predefined reduced pressure to tissue, while providing detection and notification of certain anomalous system conditions with fewer components than prior systems.

It should be apparent from the foregoing that an invention having significant advantages has been provided. While the invention is shown in only a few of its forms, it is not just limited but is susceptible to various changes and modifications without departing from the spirit thereof.

We claim:

1. An apparatus for managing reduced pressure delivered to a tissue site, the apparatus comprising:
   a pump adapted to provide a supply pressure for application of reduced pressure to the tissue site;
   a motor coupled to said pump and operable to propel said pump at varying motor speeds in response to a pressure load of said pump on said motor;
   a power source electrically coupled to said motor and adapted to receive a targeted pressure and provide a motor current selected in response to the targeted pressure and having a magnitude controlled to be substantially constant during operation of said motor, and wherein the motor has a motor voltage having a voltage magnitude that varies during operation with the pressure load and the motor speed; and
   a controller adapted to measure the voltage magnitude to provide a measured voltage magnitude for comparison to a predetermined range of voltages corresponding to selected values for maintaining the supply pressure proximate the targeted pressure, and determine whether the measured voltage magnitude is within the predetermined range of voltages.

2. The apparatus of claim 1, wherein said motor is a direct-current motor.

3. An apparatus for managing reduced pressure delivered to a tissue site, the apparatus comprising:
   a pump adapted to provide a supply pressure for the application of reduced pressure to the tissue site;
   a motor coupled to said pump to propel said pump at varying speeds in response to a the pressure load of said pump on said motor, wherein said direct-current motor is a brushed, direct-current motor; and
   a drive system electrically coupled to said motor and including (a) a power source adapted to provide direct-current power to said motor at a motor current selected in response to a targeted pressure and being substantially constant for said pump to supply the targeted pressure and at a motor voltage varying with the pressure load of said pump on said motor, and (b) a controller adapted to measure the motor voltage, and determine whether the motor voltage is within a predetermined range of voltages necessary for maintaining the supply pressure proximate the targeted pressure.

4. The apparatus of claim 3, wherein said pump is a diaphragm pump.

5. The apparatus of claim 3, wherein said drive system further comprises input circuitry to adjust the motor current to a value corresponding to the targeted pressure.

6. The apparatus of claim 3, wherein a lower boundary of the predetermined range of voltages is a stall voltage corresponding to a stall speed of said motor that occurs when the supply pressure proximate the targeted pressure, and wherein the controller is further adapted to stop said motor for a predetermined time period when the voltage magnitude is less than or equal to the stall voltage.

7. The apparatus of claim 6, wherein the controller comprises a comparator to provide a stop signal when the voltage magnitude is less than or equal to the stall voltage, and a timer responsive to the stop signal by commencing the predetermined time period and restarting said motor after the predetermined time period.

8. The apparatus of claim 6, wherein the drive system further comprises a kick-start module responsive to the controller and adapted to periodically stop and restart said motor when the voltage magnitude is greater than the stall voltage.

9. The apparatus of claim 3, wherein an upper boundary of the predetermined range of voltages is a leak voltage corresponding to a leak speed of said motor that occurs when the supply pressure drops away from the targeted pressure, and wherein the controller is further adapted to apply additional power to said motor for a predetermined time period when the voltage magnitude is greater than or equal to the leak voltage.

10. The apparatus of claim 9, wherein the controller comprises a comparator to provide a leak signal when the voltage magnitude is greater than or equal to the leak voltage, and a timer responsive to the leak signal by commencing the predetermined time period and removing the additional power from said motor after the predetermined time period.

11. The apparatus of claim 9, wherein the drive system further comprises a kick-start module responsive to the controller and adapted to periodically stop and restart said motor when the voltage magnitude is less than the leak voltage.

12. The apparatus of claim 9, wherein the additional power is provided to said motor by increasing the motor current.

13. The apparatus of claim 9, wherein the additional power is provided to said motor by increasing the voltage magnitude.

14. The apparatus of claim 3, wherein the power source further comprises a power-on module to apply additional power to said motor for a fixed time period when the motor current is first applied to said motor at start-up, whereby said motor speeds up for the fixed time period at start-up so that the supply pressure more quickly reaches the targeted pressure.

15. The apparatus of claim 14, wherein the drive system further comprises a kick-start module responsive to the controller and adapted to periodically stop and restart said motor after the fixed time period at start-up.

16. The apparatus of claim 14, wherein the additional power is provided to said motor by increasing the motor current.

17. The apparatus of claim 14, wherein the additional power is provided to said motor by increasing the voltage magnitude.

18. The apparatus of claim 3, wherein the drive system further comprises a kick-start module responsive to the controller and adapted to periodically stop and restart said motor when the voltage magnitude is within the predetermined range of voltages.

19. The apparatus of claim 18, wherein the power source is further adapted to apply additional power to said motor for a predetermined time period to restart said motor when the voltage magnitude is within the predetermined range of voltages.

20. The apparatus of claim 3, further comprising:
a pressure sensor for measuring the reduced pressure applied by said pump proximate to the tissue site; and
a comparator for comparing the supply pressure to the reduced pressure proximate the tissue site.

21. An apparatus for managing reduced pressure delivered to a tissue site, the apparatus comprising:
a pump adapted to provide a supply pressure for application of reduced pressure to the tissue site;
a direct-current motor coupled to said pump and operable to propel said pump at varying motor speeds in response to a pressure load of said pump on said motor;
a power source electrically coupled to said motor to receive a targeted pressure and provide a motor current that is selected in response to the targeted pressure and having a magnitude controlled to be substantially constant during operation of said motor, and wherein a voltage magnitude of a motor voltage across said motor varies during operation with the pressure load and the motor speed; and
a controller electrically coupled to said power source and adapted to measure the voltage magnitude, and determine whether the measured voltage magnitude is within a predetermined range of voltages corresponding to a range of voltage magnitudes for maintaining the supply pressure proximate the targeted pressure.

22. The apparatus of claim 21, wherein a lower boundary of the predetermined range of voltages is a stall voltage corresponding to a stall speed of said motor that occurs when the supply pressure proximate the targeted pressure, and wherein the controller is further adapted to stop said motor for a predetermined time period when the voltage magnitude is less than or equal to the stall voltage.

23. The apparatus of claim 21, wherein an upper boundary of the predetermined range of voltages is a leak voltage corresponding to a leak speed of said motor that occurs when the supply pressure drops away from the targeted pressure, and wherein the controller is further adapted to apply additional power to said motor for a predetermined time period when the voltage magnitude is greater than or equal to the leak voltage.

24. The apparatus of claim 21, wherein a lower boundary of the predetermined range of voltages is a stall voltage corresponding to a stall speed of said motor that occurs when the supply pressure proximate the targeted pressure and an upper boundary of the predetermined range of voltages is a leak voltage corresponding to a leak speed of said motor that occurs when the supply pressure drops away from the targeted pressure, and wherein the controller is further adapted to stop said motor for a predetermined stop time period when the voltage magnitude is less than or equal to the stall voltage and apply additional power to said motor for a predetermined leak time period when the voltage magnitude is greater than or equal to the leak voltage.

25. The apparatus of claim 24, wherein the additional power is provided to said motor by increasing the motor current.

26. The apparatus of claim 24, wherein the additional power is provided to said motor by increasing the voltage magnitude.

27. The apparatus of claim 24, comprising a kick-start module responsive to the controller and adapted to periodically stop and restart said motor when the voltage magnitude is greater than the stall voltage and less than the leak voltage.

28. The apparatus of claim 24, wherein the power source further comprises a power-on module to apply additional power to said motor for a fixed time period when the motor current is first applied to said motor at start-up, whereby said motor speeds up for the fixed time period at start-up so that the supply pressure more quickly reaches the targeted pressure.

29. The apparatus of claim 28, further comprising a kick-start module responsive to the controller and adapted to periodically stop and restart said motor after the fixed time period at start-up when the voltage magnitude is greater than the stall voltage and less than the leak voltage.

30. The apparatus of claim 24 further comprising:
a pressure sensor for measuring the reduced pressure applied by said pump proximate to the tissue site; and
a comparator for comparing the supply pressure to the reduced pressure proximate the tissue site.

31. A method for managing reduced pressure delivered to a tissue site, the method comprising:
providing a supply pressure from a pump for application of reduced pressure to the tissue site;
propelling the pump with a direct-current motor at varying motor speeds in response to a pressure load of the pump on the direct-current motor;
providing electrical power to the direct-current motor at a motor current that is selected in response to a targeted pressure and having a magnitude controlled to be substantially constant for said pump to supply the targeted pressure during operation of said motor;
measuring a voltage magnitude of a motor voltage across the direct-current motor, wherein the voltage magnitude varies during operation with the pressure load of said pump on said motor and the motor speed; comparing the measured voltage magnitude to a predetermined range of voltages; and determining whether the measured voltage magnitude is within a predetermined range of voltages corresponding to voltage magnitudes for maintaining the supply pressure proximate the targeted pressure.

32. The apparatus of claim 1, wherein a lower boundary of the predetermined range of voltages is a stall voltage corresponding to a stall speed of said motor that occurs when the supply pressure proximate the targeted pressure.

33. The apparatus of claim 32, wherein the controller is further adapted to stop said motor for a predetermined time period when the voltage magnitude is less than or equal to the stall voltage.

34. The apparatus of claim 1, wherein an upper boundary of the predetermined range of voltages is a leak voltage corresponding to a leak speed of said motor that occurs when the supply pressure drops away from the targeted pressure.

35. The apparatus of claim 34, wherein the controller is further adapted to apply additional power to said motor for a predetermined time period when the voltage magnitude is greater than or equal to the leak voltage.

36. The apparatus of claim 1, further comprising:
- a pressure sensor for measuring the reduced pressure applied by said pump proximate to the tissue site; and
- a comparator for comparing the supply pressure to the reduced pressure proximate the tissue site.

* * * * *